US006551836B1

(12) United States Patent
Chow et al.

(10) Patent No.: US 6,551,836 B1
(45) Date of Patent: Apr. 22, 2003

(54) MICROFLUIDIC DEVICES, SYSTEMS AND METHODS FOR PERFORMING INTEGRATED REACTIONS AND SEPARATIONS

(75) Inventors: Andrea W. Chow, Los Altos, CA (US); Anne R. Kopf-Sill, Portola Valley, CA (US); J. Wallace Parce, Palo Alto, CA (US); Steven A. Sundberg, San Francisco, CA (US)

(73) Assignee: Caliper Technologies Corp., Mountain View, CA (US)

(*) Notice: Subject to any disclaimer, the term of this patent is extended or adjusted under 35 U.S.C. 154(b) by 0 days.

(21) Appl. No.: 09/442,073

(22) Filed: Nov. 15, 1999

Related U.S. Application Data

(63) Continuation of application No. PCT/US99/12842, filed on Jun. 7, 1999, and a continuation-in-part of application No. 09/093,489, filed on Jun. 8, 1998, now Pat. No. 6,274,089.
(60) Provisional application No. 60/108,628, filed on Nov. 16, 1998.

(51) Int. Cl.$^7$ ............................................. G01N 27/447
(52) U.S. Cl. .................. 436/149; 204/451; 204/453; 435/7.1; 435/7.2; 435/7.4; 436/52; 436/172; 436/177; 436/180
(58) Field of Search ................................ 436/177, 180, 436/52, 149, 161, 172; 204/451, 453; 435/7.1, 7.2, 7.4

(56) References Cited

U.S. PATENT DOCUMENTS

| 4,390,403 A | 6/1983 | Batchelder |
| 4,908,112 A | 3/1990 | Pace |
| 5,110,424 A | 5/1992 | Chin |

(List continued on next page.)

FOREIGN PATENT DOCUMENTS

| WO | WO 9604547 | 2/1996 |
| WO | WO 9702357 | 1/1997 |
| WO | WO 9800231 | 1/1998 |

(List continued on next page.)

OTHER PUBLICATIONS

Cohen, C.B. et al., "A Microchip–Based Enzyme Assay for Protein Kinase A," *Anal. Chem.* (1999) 273:89–97.
Sundberg, S. A., "High–throughput and ultra–high–throughput screening: solution —and cell–based approches," *Current Opinions in Biotechnology* 2000, 11:47–53.
Dasgupta, P.K. et al., "Electroosmosis: A Reliable Fluid Propulsion System for Flow Injection Analysis," *Anal. Chem.* 66:1792–1798 (1994).
Jacobson, S.C. et al., "Fused Quartz Substrates for Microchip Electrophoresis," *Anal. Chem.* 67:2059–2063 (1995).
Manz, A. et al., "Electroosmotic pumping and electrophoretic separations for miniaturized chemical analysis systems," *J. Micromech. Microeng.* 4:257–265 (1994).
Ramsey, J.M. et al., "Microfabricated chemical measurement systems," *Nature Med.* 1:1093–1096 (1995).

(List continued on next page.)

*Primary Examiner*—Jan Ludlow
(74) *Attorney, Agent, or Firm*—Gwynedd Warren; Andrew L. Filler; Angela P. Horne

(57) ABSTRACT

Microfluidic devices for performing integrated reaction and separation operations. The devices have a planar substrate having a first surface with an integrated channel network disposed therein. The reaction region in the integrated microscale channel network has a mixture of at least first and second reactants located therein, wherein the mixture interacts to produce one or more products. The reaction region is configured to maintain contact between the first and second reactants contained within it. The device also includes a separation region in the integrated channel network, where the separation region is configured to separate the first reactant from the product, when the first reactant and product are flowing through the separation region.

22 Claims, 16 Drawing Sheets

U.S. PATENT DOCUMENTS

| | | |
|---|---|---|
| 5,126,022 A | 6/1992 | Soane et al. |
| 5,264,101 A | 11/1993 | Demorest et al. |
| 5,480,614 A | 1/1996 | Kamahori |
| 5,498,392 A | 3/1996 | Wilding et al. |
| 5,571,410 A | 11/1996 | Swedberg et al. |
| 5,585,069 A | 12/1996 | Zanzucchi et al. |
| 5,587,128 A | 12/1996 | Wilding et al. |
| 5,593,838 A | 1/1997 | Zanzucchi et al. |
| 5,599,432 A | 2/1997 | Manz et al. |
| 5,603,351 A | 2/1997 | Cherukuri et al. |
| 5,632,957 A | 5/1997 | Heller et al. |
| 5,635,358 A | 6/1997 | Wilding et al. |
| 5,637,469 A | 6/1997 | Wilding et al. |
| 5,660,703 A | 8/1997 | Dasgupta |
| 5,699,157 A | 12/1997 | Parce |
| 5,750,015 A | 5/1998 | Soane et al. |
| 5,770,029 A | 6/1998 | Nelson et al. |
| 5,779,868 A | 7/1998 | Parce et al. |
| 5,800,690 A | 9/1998 | Chow et al. |
| 5,810,985 A | 9/1998 | Bao et al. |
| 5,842,787 A | 12/1998 | Kopf-Sill et al. |
| 5,852,495 A | 12/1998 | Parce |
| 5,869,004 A | 2/1999 | Parce et al. |
| 5,876,675 A | 3/1999 | Kennedy |
| 5,880,071 A | 3/1999 | Parce et al. |
| 5,882,465 A | 3/1999 | McReynolds |
| 5,885,470 A | 3/1999 | Parce et al. |
| 5,922,591 A * | 7/1999 | Anderson et al. |
| 5,942,443 A | 8/1999 | Parce et al. |
| 5,948,227 A | 9/1999 | Dubrow |
| 5,955,028 A | 9/1999 | Chow |
| 5,957,579 A | 9/1999 | Kopf-Sill et al. |
| 5,958,203 A | 9/1999 | Parce et al. |
| 5,958,694 A | 9/1999 | Nikiforov |
| 5,959,291 A | 9/1999 | Jensen |
| 5,964,995 A | 10/1999 | Nikiforov et al. |
| 5,965,001 A | 10/1999 | Chow et al. |
| 5,965,410 A | 10/1999 | Chow et al. |
| 5,972,187 A | 10/1999 | Parce et al. |
| 5,976,336 A | 11/1999 | Dubrow et al. |
| 5,989,402 A | 11/1999 | Chow et al. |
| 6,001,231 A | 12/1999 | Kopf-Sill |
| 6,004,515 A | 12/1999 | Parce et al. |
| 6,011,252 A | 1/2000 | Jensen |
| 6,012,902 A | 1/2000 | Parce |
| 6,042,721 A | 3/2000 | Dubrow |
| 6,046,056 A | 4/2000 | Parce et al. |
| 6,318,970 B1 * | 11/2001 | Backhouse |

FOREIGN PATENT DOCUMENTS

| | | |
|---|---|---|
| WO | WO 9800705 | 1/1998 |
| WO | WO 98/00707 | 1/1998 |
| WO | WO 98/02728 | 1/1998 |
| WO | WO 98/05424 | 2/1998 |
| WO | WO 98/22811 | 5/1998 |
| WO | WO 98/45481 | 10/1998 |
| WO | WO 98/45929 | 10/1998 |
| WO | WO 98/46438 | 10/1998 |
| WO | WO 98/49548 | 11/1998 |
| WO | WO 98/55852 | 12/1998 |
| WO | WO 98/56956 | 12/1998 |
| WO | WO 99/00649 | 1/1999 |
| WO | WO 99/10735 | 3/1999 |
| WO | WO 99/12016 | 3/1999 |
| WO | WO 99/16162 | 4/1999 |
| WO | WO 99/19056 | 4/1999 |
| WO | WO 99/19516 | 4/1999 |
| WO | WO 99/29497 | 6/1999 |
| WO | WO 99/56954 | 11/1999 |
| WO | WO 00/09753 | 2/2000 |

OTHER PUBLICATIONS

Seiler, K. et al., "Planar Glass Chips for Capillary Electrophoresis: Repetitive Sample Injection, Quantitation, and Separation Efficiency," *Anal. Chem.* 65:1481–1488 (1993).

Seiler, K. et al., "Electroosmotic Pumping and Valveless Control of Fluid Flow Within a Manifold of Capillaries on a Glass Chip," *Anal. Chem.* 66:3485–3491 (1994).

* cited by examiner

MICROFLUIDIC DEVICES, SYSTEMS AND METHODS FOR PERFORMING INTEGRATED REACTIONS AND SEPARATIONS

CROSS REFERENCE TO RELATED APPLICATIONS

This application is a continuation of PCT application No. PCT/US99/12842, filed Jun. 7, 1999 and a continuation-in-part of U.S. Ser. No. 09/093,489 filed Jun. 8, 1998 now U.S. Pat. 6,274,089 and a non-provisional of U.S. Ser. No. 60/108,628 filed Nov. 16, 1998, the disclosures of which are incorporated by reference for all purposes.

BACKGROUND OF THE INVENTION

In the analysis of biological and chemical systems, a number of advantages are realized by the process of miniaturization. For example, by miniaturizing analytical and synthetic processes, one obtains advantages in: (1) reagent volumes, where reagents are rare and/or expensive to produce or purchase; (2) reaction times, where mixing or thermal modulation of reactants is a rate limiting parameter; and (3) integration, allowing one to combine multiple preparative and analytical/synthetic operations in a single bench-top unit.

Despite the advantages to be obtained through miniaturized laboratory systems, or microfluidic systems, early attempts at developing such systems suffered from a number of problems. Of particular note was the inability of early systems to control and direct fluid movement through microfluidic channels and chambers in order to mix, react and separate reaction components for analysis. Specifically, many of the early microfluidic systems utilized micromechanical fluid direction system, e.g., microfabricated pumps, valves and the like, which were expensive to fabricate and required complex control systems to be properly operated. Many of these systems also suffered from dead volumes associated with the mechanical elements, which prevented adequate fluid control substantially below the microliter or 100 nanoliter range. Pneumatic systems were also developed to move fluids through microfluidic channels, which systems were simpler to operate. Again, however, these systems lacked sufficient controllability to move small, precise amounts of fluids.

Pioneering developments in controlled electrokinetic material transport have subsequently allowed for the precise control and manipulation of extremely small amounts of fluids and other materials within interconnected channel structures, without the need for mechanical valves and pumps. See Published International Patent Application No. WO 96/04547, to Ramsey. In brief, by concomitantly controlling electric fields in a number of intersecting channels, one can dictate the direction of flow of materials and/or fluids at an unvalved intersection.

These advances in material transport and direction within microfluidic channel networks have provided the ability to perform large numbers of different types of operations within such networks. See, e.g., commonly owned Published International Application No. 98/00231 to Parce et al., and Published International Application No. 98/00705, describing the use of such systems in performing high-throughput screening operations.

Despite the wide-ranging utility and relative simplicity of these advances, in some cases, it may be desirable to provide simpler solutions to material transport needs within a microfluidic system. The present invention meets these and other needs.

In particular, the present invention provides material direction methods and systems that take advantage of certain flow properties of the materials, in conjunction with novel structures, to controllably direct material flow through an integrated microfluidic channel structure.

SUMMARY OF THE INVENTION

In a first aspect, this invention provides a microfluidic device for performing integrated reaction and separation operations. The device comprises a body structure having an integrated microscale channel network disposed therein. The reaction region within the integrated microscale channel network has a mixture of at least first and second reactants disposed in and flowing through the reaction region, wherein the mixture interacts to produce one or more products. The reaction region is configured to maintain contact between the first and second reactants flowing therethrough. The device also includes a separation region in the integrated channel network, where the separation region is in fluid communication with the reaction region and is configured to separate the first reactant from the one or more products flowing therethrough.

The invention also provides a device for performing integrated reaction and separation operations. The device comprises a planar substrate having a first channel disposed in the substrate containing at least first and second fluid regions. The first fluid region has an ionic concentration higher than an ionic concentration of the second fluid region, and the first and second fluid regions communicates at a first fluid interface. Second and third channels are disposed in the substrate, the second channel intersects and connects the first and third channels at intermediate points along a length of the first and third channels, respectively. The device also includes an electrokinetic material transport system for applying a voltage gradient along a length of the first channel, but not the second channel which electrokinetically moves the first fluid interface past the intermediate point of the first channel and forces at least a portion of the first fluid regions through the second channel into the third channel.

This invention also provides methods of performing integrated reaction and separation operations which include providing a microfluidic device comprising a body structure having a reaction channel and a separation channel disposed therein, the reaction channel and separation channel being in fluid communication. At least first and second reactants flow through the reaction channel in a first fluid region. The first and second reactants interact to form at least a first product within the first fluid region. The step of transporting through the first channel is carried out under conditions for maintaining the first and second reactants and products substantially within the first fluid region. At least a portion of the first fluid region is directed to the separation channel, which is configured to separate the product from at least one of the first and second reactants. The portion is then transported along the separation channel to separate the product from at least the first reactant.

The invention also provides methods of directing fluid transport in a microscale channel network comprising a microfluidic device having at least first and second intersecting channels disposed therein, the first channel being intersected by the second channel at an intermediate point. First and second fluid regions are introduced into the first channel, wherein the first and second fluid regions are in communication at a first fluid interface, and wherein the first fluid region has a higher conductivity than the second fluid region. An electric field is applied across a length of the first channel, but not across the second channel, to electroosmotically transport the first and second fluid regions through the first channel past the intermediate point, whereby a portion of the first fluid is forced into the second channel.

The invention also provides methods of transporting materials in an integrated microfluidic channel network comprising a first microscale channel that is intersected at an intermediate point by a second channel. First and second fluid regions are introduced serially into the first channel and are in communication at a first fluid interface. A motive force is applied to the first and second fluid regions to move the first and second fluid regions past the intermediate point. The first and second fluid regions have different flow rates or inherent velocities under said motive force. The different inherent velocities produce a pressure differential at the first interface that results in a portion of the first material being injected into the second channel.

The invention also provides methods of performing integrated reaction and separation operations in a microfluidic system, comprising a microfluidic device with a body, a reaction channel, and a separation channel disposed therein. The reaction channel is in fluid communication with the separation channel. At least first and second reactants are transported through the first region. The first and second reactants are maintained substantially together to allow reactants to interact to form at least a first product in the first mixture. The first mixture, including the product, is transported to the second region wherein the product is separated from at least one of the reactants.

The invention also provides methods of performing integrated reaction and separation operations in a microfluidic system, comprising a microfluidic device having at least first and second channel regions disposed therein, the first and second channel regions are connected by a first connecting channel. First reactants are introduced into the first channel region, the first reactants being contained within a first material region having a first ionic concentration. The first region is bounded by second regions having a second ionic concentration, the second ionic concentration is lower than the first ionic concentration. The first and second material regions are transported past an intersection of the first channel region and the first connecting channel, whereby at least a portion of the first material region is diverted through the connecting channel and into the second channel region.

In related aspects, the present invention also provides microfluidic devices for analyzing electrokinetic mobility shifts of analytes, where the device includes a body structure having a first microfluidic channel portion disposed therein, where the first channel portion has substantially no electrical field applied across its length. A second microfluidic channel portion is also included, but where the second channel portion has an electrical field applied across its length. The second channel portion being fluidly connected to the first channel portion. The device also includes a pressure source in communication with at least one of the first channel portion and the second channel portion for moving a material through the first channel portion into the second channel portion.

Relatedly, the present invention also provides methods of analyzing materials using the described devices. In particular, the methods of the invention analyze an effect of a first analyte on a second analyte. The methods steps include contacting the first analyte with the second analyte in a first microfluidic channel portion having substantially no electric field applied across its length. At least a portion of the first analyte and second analyte is transported to a second channel portion that is in fluid communication with the first channel portion and which has an electric field applied across its length. A change in the electrokinetic mobility of the second analyte, if any, is measured in the second channel portion, where a change in the electrokinetic mobility of the second analyte is indicative of an effect of the first analyte on the second analyte.

Similarly provided are methods of analyzing an electrokinetic mobility shift in a first analyte, which methods comprise flowing the first analyte through a first microscale channel portion having substantially no electrical field applied across it. The first analyte is then introduced into a second microfluidic channel portion. An electric field is then applied across a length of the second microfluidic channel portion but not across the length of the first a microfluidic channel portion. Finally, an electrokinetic mobility of the first analyte is measured under the electric field applied in the second channel portion.

BRIEF DESCRIPTION OF THE FIGURES

FIG. 3 illustrates an example of an embodiment of a microfluidic device of the present invention for performing integrated reaction and separation operations. FIG. 3A illustrates the elements of the device itself, while

FIG. 4 illustrates one alternate embodiment of a microfluidic device according to the present invention for performing integrated reaction and separation operations. FIG. 4A illustrates the elements of the device itself, while

FIG. 10 schematically illustrates alternate devices for carrying out integrated reaction and separation operations. FIG. 10a illustrates an integrated colinear channel for performing reactions and separations under pressure and electrokinetic flow, while

DETAILED DESCRIPTION OF THE INVENTION

I. General

A. Desirability for Integration

Figure 1:
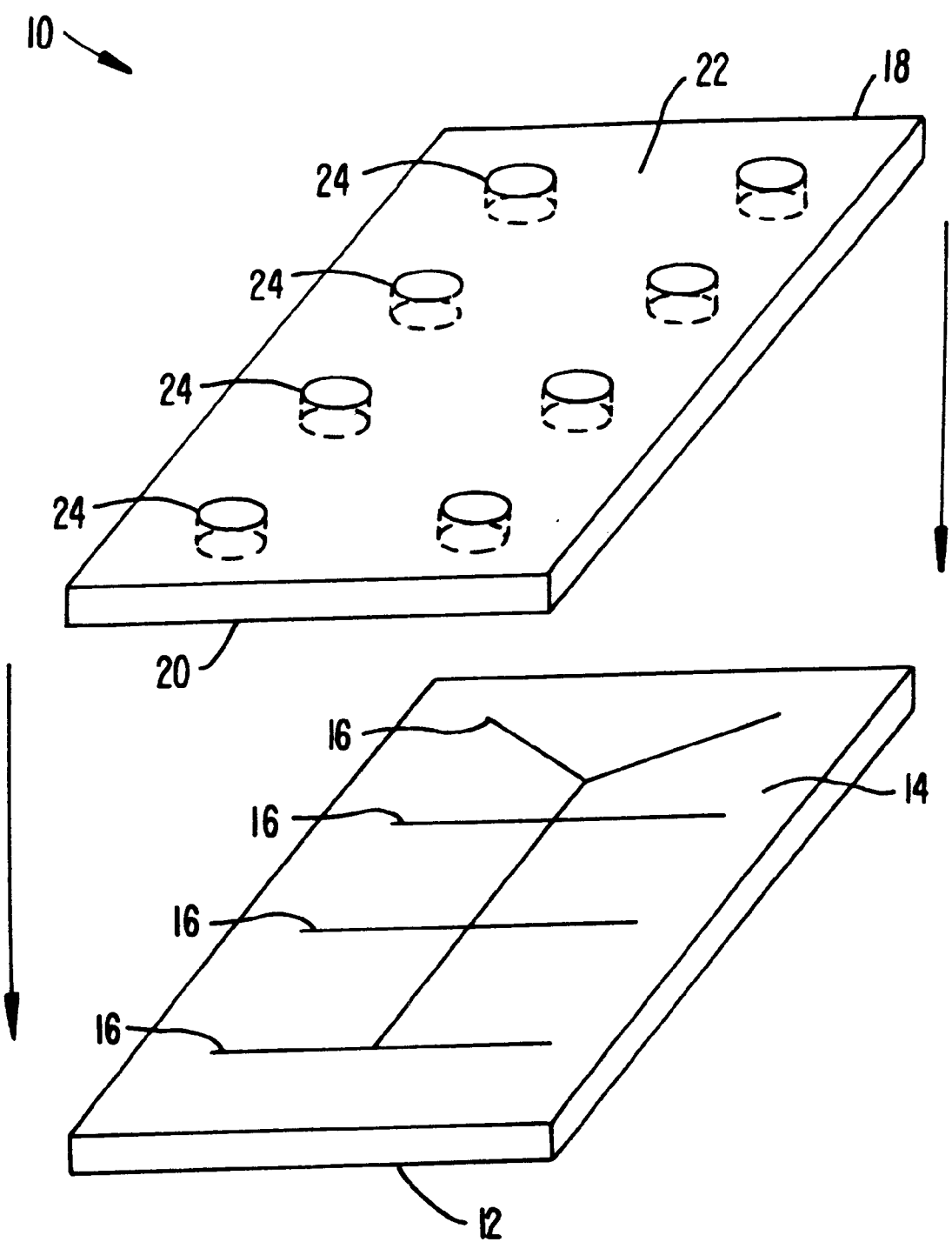
FIG. 1 schematically illustrates an example of a microfluidic device incorporating a layered body structure.

In chemical and biochemical analyses, a number of useful analytical operations require processes that include two or more operational steps. For example, many operations require that a sample material undergo some preparative reaction(s) prior to the ultimate analytical operation. Alternatively, some analytical operations require multiple different process steps in the ultimate analytical operation. As a specific example, a large number of operations require a reaction step and a separation step, which depending upon the analytical operation, may be in either order. Such operations are easily carried out where one is operating at the bench scale, e.g., utilizing reagent volumes well in excess of 5 or 10 $\mu$l, permitting the use of conventional fluid handling equipment and technology.

However, when operating in the microfluidic range, e.g., on the submicroliter to nanoliter level, conventional fluid handling technologies fail. Specifically, conventional fluidic systems, e.g., pipettors, tubing, pumps, valves, injectors, and the like, are incapable of transporting, dispensing and/or measuring reagent volumes in the submicroliter, nanoliter or picoliter range. While microfluidic technology provides potential avenues for addressing many of these issues, early proposals in microfluidics lacked the specific control to optimize such systems. For example, a great deal of microfluidic technology to date has been developed using mechanical fluid and material transport systems, e.g., microfabricated pumps and valves, pneumatic or hydraulic systems, acoustic systems, and the like. These technologies all suffer from problems of inaccurate fluid control, as well as excessive volume requirements, e.g., in pump and valve dead volumes. Failing in this regard, such systems are largely inadequate for performing multiple integrated operations on microfluidic scale fluid or reagent volumes.

The present invention, on the other hand, provides microfluidic systems that have precise fluidic control at the submicroliter, nanoliter and even picoliter range. Such control permits the ready integration of multiple operations within a single microfluidic device, and more particularly, the integration of a reaction operation and a separation operation, within a single device. Further, microfluidic systems of the present invention, that incorporate such control also offer advantages of automatability, low cost and high or ultra-high-throughput.

In a particular aspect, the microfluidic devices and systems of the invention include microscale or microfluidic channel networks that comprise a reaction region and a separation region. These two regions are connected to allow the controlled movement of material from one region to the other. As noted above, this is made simpler by precise control of material transport within the channel network. In particularly preferred aspects, material transport is carried out using a controlled electrokinetic material transport system. In alternate preferred aspects, combined pressure-based and electrokinetic transport systems are used.

As used herein, the term "microfluidic" generally refers to one or more fluid passages, chambers or conduits which have at least one internal cross-sectional dimension, e.g., depth, width, length, diameter, etc., that is less than 500 $\mu$m, and typically between about 0.1 $\mu$m and about 500 $\mu$m. In the devices of the present invention, the microscale channels or chambers preferably have at least one cross-sectional dimension between about 0.1 $\mu$m and 200 $\mu$m, more preferably between about 0.1 $\mu$m and 100 $\mu$m, and often between about 1 $\mu$m and 20 $\mu$m. Accordingly, the microfluidic devices or systems prepared in accordance with the present invention typically include at least one microscale channel, usually at least two intersecting microscale channels, and often, three or more intersecting channels disposed within a single body structure. Channel intersections may exist in a number of formats, including cross intersections, "T" intersections, or any number of other structures whereby two channels are in fluid communication.

The microfluidic devices of the present invention typically employ a body structure that has the integrated microfluidic channel network disposed therein. In preferred aspects, the body structure of the microfluidic devices described herein typically comprises an aggregation of two or more separate layers which when appropriately mated or joined together, form the microfluidic device of the invention, e.g., containing the channels and/or chambers described herein. Typically, the microfluidic devices described herein will comprise a top portion, a bottom portion, and an interior portion, wherein the interior portion substantially defines the channels and chambers of the device.

FIG. 1 illustrates a general example of a two-layer body structure 10, for a microfluidic device. In preferred aspects, the bottom portion of the device 12 comprises a solid substrate that is substantially planar in structure, and which has at least one substantially flat upper surface 14. A variety of substrate materials may be employed as the bottom portion. Typically, because the devices are microfabricated, substrate materials will be selected based upon their compatibility with known microfabrication techniques, e.g., photolithography, wet chemical etching, laser ablation, air abrasion techniques, injection molding, embossing, and other techniques. The substrate materials are also generally selected for their compatibility with the full range of conditions to which the microfluidic devices may be exposed, including extremes of pH, temperature, salt concentration, and application of electric fields. Accordingly, in some preferred aspects, the substrate material may include materials normally associated with the semiconductor industry in which such microfabrication techniques are regularly employed, including, e.g., silica based substrates, such as glass, quartz, silicon or polysilicon, as well as other substrate materials, such as gallium arsenide and the like. In the case of semiconductive materials, it will often be desirable to provide an insulating coating or layer, e.g., silicon oxide, over the substrate material, and particularly in those applications where electric fields are to be applied to the device or its contents.

In additional preferred aspects, the substrate materials will comprise polymeric materials, e.g., plastics, such as polymethylmethacrylate (PMMA), polycarbonate, polytetrafluoroethylene (TEFLON™), polyvinylchloride (PVC), polydimethylsiloxane (PDMS), polysulfone, polystyrene, polymnethylpentene, polypropylene, polyethylene, polyvinylidine fluoride, ABS (acrylonitrile-butadiene-styrene copolymer), and the like. Such polymeric substrates are readily manufactured using available microfabrication techniques, as described above, or from microfabricated masters, using well known molding techniques, such as injection molding, embossing or stamping, or by polymerizing the polymeric precursor material within the mold (See U.S. Pat. No. 5,512,131). Such polymeric substrate materials are preferred for their ease of manufacture, low cost and disposability, as well as their general inertness to most extreme reaction conditions. Again, these polymeric materials may include treated surfaces, e.g., derivatized or coated surfaces, to enhance their utility in the microfluidic system, e.g., provide enhanced fluid direction, e.g., as described in U.S. patent application Ser. No. 08/843,212, filed Apr. 14, 1997, now U.S. Pat. No. 5,885,470 and which is incorporated herein by reference in its entirety for all purposes.

The channels and/or chambers of the microfluidic devices are typically fabricated into the upper surface of the bottom substrate or portion 12, as microscale grooves or indentations 16, using the above described microfabrication techniques. The top portion or substrate 18 also comprises a first planar surface 20, and a second surface 22 opposite the first planar surface 20. In the microfluidic devices prepared in accordance with the methods described herein, the top portion also includes a plurality of apertures, holes or ports 24 disposed therethrough, e.g., from the first planar surface 20 to the second surface 22 opposite the first planar surface.

The first planar surface 20 of the top substrate 18 is then mated, e.g., placed into contact with, and bonded to the planar surface 14 of the bottom substrate 12, covering and sealing the grooves and/or indentations 16 in the surface of the bottom substrate, to form the channels and/or chambers (i.e., the interior portion) of the device at the interface of these two components. The holes 24 in the top portion of the device are oriented such that they are in communication with at least one of the channels and/or chambers formed in the interior portion of the device from the grooves or indentations in the bottom substrate. In the completed device, these holes function as reservoirs for facilitating fluid or material introduction into the channels or chambers of the interior portion of the device, as well as providing ports at which electrodes may be placed into contact with fluids within the device, allowing application of electric fields along the channels of the device to control and direct fluid transport within the device.

In many embodiments, the microfluidic devices will include an optical detection window disposed across one or more channels and/or chambers of the device. Optical detection windows are typically transparent such that they are capable of transmitting an optical signal from the channel/ chamber over which they are disposed. Optical detection windows may merely be a region of a transparent cover layer, e.g., where the cover layer is glass or quartz, or a transparent polymer material, e.g., PMMA, polycarbonate, etc. Alternatively, where opaque substrates are used in manufacturing the devices, transparent detection windows fabricated from the above materials may be separately manufactured into the device.

These devices may be used in a variety of applications, including, e.g., the performance of high throughput screening assays in drug discovery, immunoassays, diagnostics, genetic analysis, and the like. As such, the devices described herein, will often include multiple sample introduction ports or reservoirs, for the parallel or serial introduction and analysis of multiple samples. In preferred aspects, however, these devices are coupled to a sample introduction port, e.g., a pipettor, which serially introduces multiple samples into the device for analysis. Examples of such sample introduction systems are described in e.g., Published International Patent Application Nos. WO 98/00231 and 98/00707, each of which is hereby incorporated by reference in its entirety for all purposes.

As described above, the devices and systems of the present invention preferably employ electrokinetic transport systems for manipulating fluids and other materials within the microfluidic channel networks. As used herein, "electrokinetic material transport systems" include systems which transport and direct materials within an interconnected channel and/or chamber containing structure, through the application of electrical fields to the materials, thereby causing material movement through and among the channel and/or chambers, i.e., positively charged species will generally be attracted to the negative electrode, while negative ions will be attracted to the positive electrode.

Such electrokinetic material transport and direction systems include those systems that rely upon the electrophoretic mobility of charged species within the electric field applied to the structure. Such systems are more particularly referred to as electrophoretic material transport systems. Other electrokinetic material direction and transport systems rely upon the electroosmotic flow of fluid and material within a channel or chamber structure which results from the application of an electric field across such structures. In brief, when a fluid is placed into a channel which has a surface bearing charged functional groups, e.g., hydroxyl groups in etched glass channels or glass microcapillaries, those groups can ionize. In the case of hydroxyl functional groups, this ionization, e.g., at neutral pH, results in the release of protons from the surface and into the fluid, creating a concentration of protons at near the fluid/surface interface, or a positively charged sheath surrounding the bulk fluid in the channel. Application of a voltage gradient across the length of the channel, will cause the proton sheath to move in the direction of the voltage drop, i.e., toward the negative electrode. Although described as electrophoretic or electroosmotic, the material transport systems used in conjunction with the present invention often rely upon a combination of electrophoretic and electroosmotic transporting forces to move materials.

"Controlled electrokinetic material transport and direction," as used herein, refers to electrokinetic systems as described above, which employ active control of the voltages applied at multiple, i.e., more than two, electrodes. Rephrased, such controlled electrokinetic systems concomitantly regulate voltage gradients applied across at least two intersecting channels. Controlled electrokinetic material transport is described in Published PCT Application No. WO 96/04547, to Ramsey, which is incorporated herein by reference in its entirety for all purposes. In particular, the preferred microfluidic devices and systems described herein, include a body structure which includes at least two intersecting channels or fluid conduits, e.g., interconnected, enclosed chambers, which channels include at least three unintersected termini. The intersection of two channels refers to a point at which two or more channels are in fluid communication with each other, and encompasses "T" intersections, cross intersections, "wagon wheel" intersections of multiple channels, or any other channel geometry where two or more channels are in such fluid communication. An unintersected terminus of a channel is a point at which a channel terminates not as a result of that channel's intersection with another channel, e.g., a "T" intersection. In preferred aspects, the devices will include at least three intersecting channels having at least four unintersected termini. In a basic cross channel structure, where a single horizontal channel is intersected and crossed by a single vertical channel, controlled electrokinetic material transport operates to controllably direct material flow through the intersection, by providing constraining flows from the other channels at the intersection. For example, assuming one was desirous of transporting a first material through the horizontal channel, e.g., from left to right, across the intersection with the vertical channel. Simple electrokinetic material flow of this material across the intersection could be accomplished by applying a voltage gradient across the length of the horizontal channel, i.e., applying a first voltage to the left terminus of this channel, and a second, lower voltage to the right terminus of this channel, or by allowing the right terminus to float (applying no voltage). However, this type of material flow through the intersection would result in a substantial amount of diffusion at the intersection, resulting from both the natural diffusive properties of the material being transported in the medium used, as well as convective effects at the intersection.

In controlled electrokinetic material transport, the material being transported across the intersection is constrained by low level flow from the side channels, e.g., the top and bottom channels. This is accomplished by applying a slight voltage gradient along the path of material flow, e.g., from the top or bottom termini of the vertical channel, toward the right terminus. The result is a "pinching" of the material flow at the intersection, which prevents the diffusion of the material into the vertical channel. The pinched volume of material at the intersection may then be injected into the vertical channel by applying a voltage gradient across the length of the vertical channel, i.e., from the top terminus to the bottom terminus. In order to avoid any bleeding over of material from the horizontal channel during this injection, a low level of flow is directed back into the side channels, resulting in a "pull back" of the material from the intersection.

In addition to pinched injection schemes, controlled electrokinetic material transport is readily utilized to create virtual valves which include no mechanical or moving parts. Specifically, with reference to the cross intersection described above, flow of material from one channel segment to another, e.g., the left arm to the right arm of the horizontal channel, can be efficiently regulated, stopped and reinitiated, by a controlled flow from the vertical channel, e.g., from the bottom arm to the top arm of the vertical channel. Specifically, in the 'off' mode, the material is transported from the left arm, through the intersection and into the top arm by applying a voltage gradient across the left and top termini. A constraining flow is directed from the bottom arm to the top arm by applying a similar voltage gradient along this path (from the bottom terminus to the top terminus). Metered amounts of material are then dispensed from the left arm into the right arm of the horizontal channel by switching the applied voltage gradient from left to top, to left to right. The amount of time and the voltage gradient applied dictates the amount of material that will be dispensed in this manner.

Figure 2:
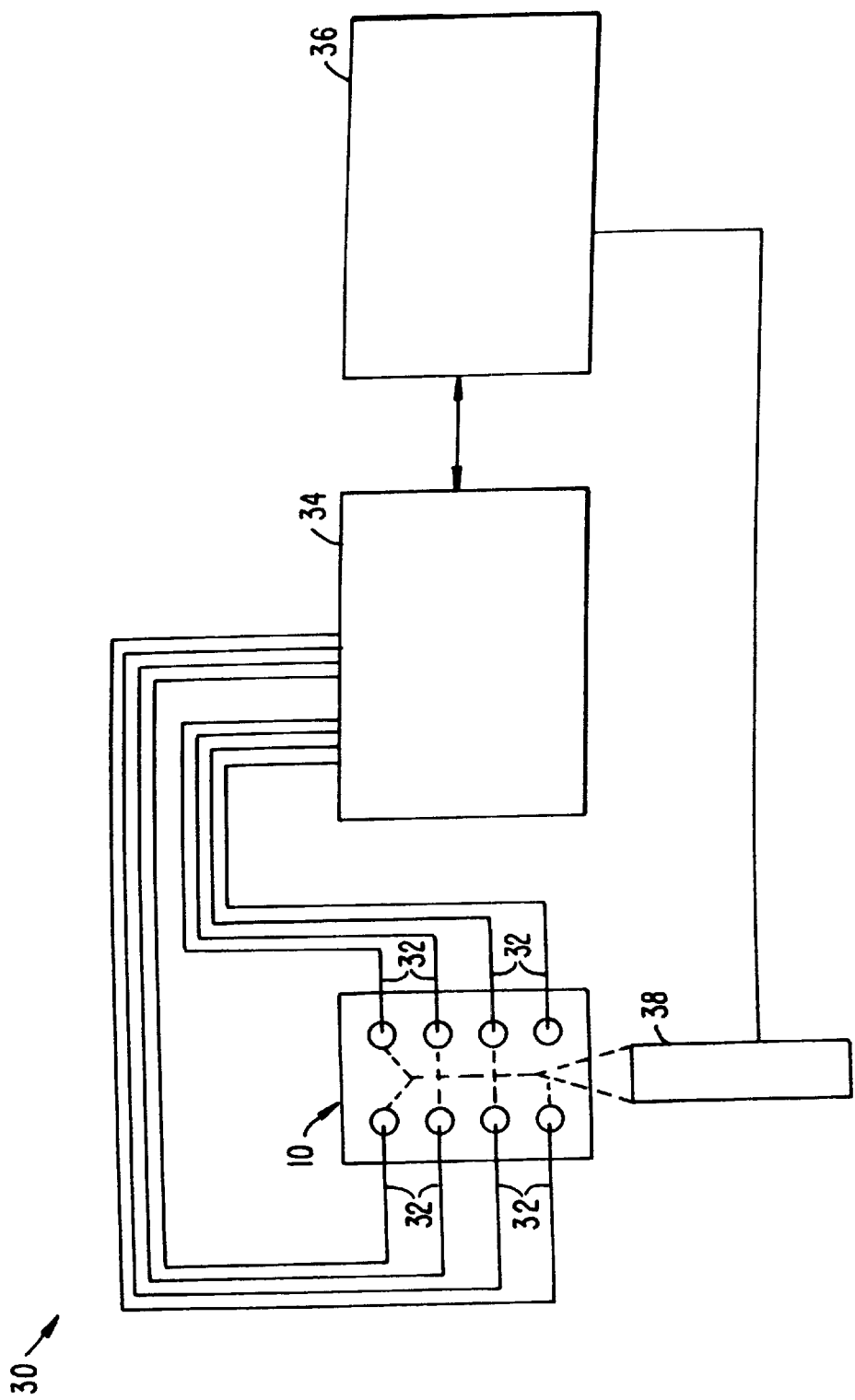
FIG. 2 schematically illustrates a control system for electrokinetically moving materials within a microfluidic device.

A schematic illustration of a system 30 for carrying out analytical operations within a microfluidic device using controlled electrokinetic material transport is illustrated in FIG. 2. As shown, the microfluidic device 10, is connected to an electrical controller 34 via a series of electrical leads/electrodes 32. The electrodes are disposed in the reservoirs that are disposed at the termini of the channels in the channel network within the device 10. The electrical controller typically includes a power supply, as well as appropriate circuitry for regulation of voltage and/or currents applied to each of the electrical leads/electrodes 32 to control material transport, as described above. One example of such a power supply is that described in commonly owned Published International Patent Application No. WO 98/00707. The system shown, also includes a computer 36, which includes appropriate software or other programming for instructing the electrical controller to apply appropriate voltage/current profiles to the various reservoirs or channel termini in order to achieve a desired material movement within the device, e.g., for a given operation. In addition to instructing the electrical controller, the computer also receives data from the controller relating to the electrical parameters within the device, e.g., applied current/voltage, resistance, etc., as well as receiving data from the detector 38. For example, in typical applications, the detector 38 is an optical, e.g., fluorescence detector, which detects relative fluorescence levels within the device and reports the data to the computer 36 for storage and subsequent analysis. The detector is generally disposed adjacent a detection window that is disposed in the device, e.g., a translucent or transparent region of the device 10. Accordingly, the computer is typically programmed to instruct the operation of the system, as well as receive, store and analyze the data generated by the system.

Although described for the purposes of illustration with respect to a four way, cross intersection, these controlled electrokinetic material transport systems can be readily adapted for more complex interconnected channel networks, e.g., arrays of interconnected parallel channels.

In alternate aspects, the present invention provides microfluidic devices, systems and methods of using them, for performing reaction and separation operations within an integrated microfluidic channel network, that utilize different material direction and transport means in order to ensure reactants in the reaction channel portion are maintained together, while reactants are allowed to separate within the separation channel portion.

As described above, the integrated device typically includes at least a first channel portion that is configured so as to maintain reactants that are flowing through it, together. In the context of the present embodiment, this is typically accomplished by driving the flow of the reactants through the first channel portion using a pressure-based flow system. By using pressure-based flow, different reactants do not suffer from biasing effects of differential electrophoretic mobilities, as is true under purely electrokinetic material transport systems. In operation, first and second analytes that are to be kept in contact are flowed along the first channel portion, or reaction channel, where that channel portion has substantially no applied electric field disposed across it. The absence of an electric field avoids the electrophoretic biasing problem noted above. A second microfluidic channel portion, in fluid communication with the first channel portion is then used to perform the separation operation. In particular, at least a portion of the reactants that are flowing through the first channel portion are introduced into the second channel portion. The second channel portion has an electric field applied across its length, in order to promote the electrophoretic separation of reactants. Application of an electric field is generally carried out as described herein, e.g., via electrodes disposed in electrical communication with the termini of the second channel portion, either directly, or via connecting channels. Typically, the materials flowing through the second channel portion have a net flow in one direction, e.g., toward the detection zone, as a result of one or both of electroosmotic flow and/or pressure based flow from the first channel. As a result, even species with electrophoretic mobilities opposite to the desired direction of flow, e.g., away from the detection zone in the second channel portion, will still have a net flow in that direction, and thereby permit their detection.

In those instances where the interaction of the first and second analytes has an electrophoretic mobility altering effect on one or both of the analytes, e.g., resulting in a product that has an electrophoretic mobility different from one or more of the original analytes, the applied electric field within the second channel portion will result in a separation of the product from the original analytes. The product is then detected, allowing a quantitative determination of the interaction of the analytes.

An exemplary assay that is carried out according to the methods of the present invention is a nonfluorogenic phosphatase assay which employs a phosphorylated fluorescent substrate that is dephosphorylated by a phosphatase enzyme to yield a more negatively charged fluorescent product. Thus, the action of the phosphatase on the phosphorylated substrate has a mobility altering effect on the dephosphorylated product. In the systems described herein, the assay is carried out by flowing the phosphatase enzyme and fluorescent phosphorylated substrate through the first channel portion by applying a pressure differential across the first channel portion, to force or draw the reactants through the channel. Because there is no electric field applied across the length of the channel, there is nothing to cause the separation of the dephosphorylated product from the phosphorylated substrate. The mixture of product, substrate and enzyme is then directed into the second channel portion which has, or is capable of having an electric field applied across its length. When subjected to the electric field, the dephosphorylated fluorescent product has a substantially different mobility within the second channel portion than the phosphorylated fluorescent substrate. As these two fluorescent components are physically separated, they are therefore, separately detectable. The production of the separately detectable species, e.g., substrate and product, is indicative that the enzyme has acted on the substrate. Assuming then that one wanted to screen a variety of materials to determine whether those materials had an effect on the phosphatase activity, it would merely require introducing those materials into the first reaction channel, one at a time, as a third reactant contacting the phosphatase enzyme and substrate. One would again measure the relative amount of fluorescent product produced, and compare it to a control reaction, e.g., where no effector of that interaction was present.

The reaction mixture is optionally introduced into the second channel portion as discrete aliquots or plugs, which are then separated to yield two separate peaks of the detected label, or as a continuous flow of the reaction mixture which produces a constant label signal which is interrupted when an effector of the desired interaction is introduced. Such continuous flow assay formats are described in great detail in Published International Patent Application No. WO98/00231, which is incorporated herein by reference. In brief, variations in the mobility of the labeled portion of the reaction mixture in discrete regions, e.g., regions where effectors (inhibitors/enhancers) are introduced, results in an accumulation or depletion of the labeled product either before or after the particular reaction region. This is due to the change in amount of product within those regions resulting from the presence of, e.g., an inhibitor, which is then made detectable by the differential mobility of product and substrate.

B. Specific Assay Examples

As noted above, a number of useful analytical operations require processes that include two or more operational steps. For example, a number of analytical assays require the performance of a reaction step followed by a separation step. This is typically the case where the activity that is sought to be detected in the assay does not itself produce a change in the level of a detectable signal, such as the production or depletion of a colored, radioactive or fluorescent species, e.g., product or substrate, an alteration in detectable solution characteristics, e.g. pH, conductivity, etc. or the like. In such cases, it is often necessary to be able to separate reactants from products in order to then distinguish between these components and determine their relative quantities.

Specific examples of analytical operations that do not produce an alteration in the level of detectable signal in a mixture of reactants and products are those assays referred to as "non-fluorogenic" or "non-chromogenic" assays. In particular, for a number of assay types, reagents are available that will produce a colored or fluorescent signal in response to a particular activity. For example, for a number of enzymes, fluorogenic or chromogenic substrates are commercially available. In the case of fluorogenic substrates, the substrate can be either non-fluorescent or have a low level of fluorescence as a substrate. Alternatively, the substrate may be fluorescent while the product is non-fluorescent or detectably less fluorescent than the substrate. However, upon reaction with the enzyme of interest, a fluorescent product is produced (or the fluorescent substrate is consumed). By measuring the amount of fluorescence produced or consumed, one can determine the relative activity of the enzyme.

Other examples of fluorogenic reactants include, e.g., nucleic acid or molecular beacons. These molecular beacons include a fluorophore/quencher pair, at different ends of a self-complementary nucleic acid sequence or at different ends of two complementary probes. In its native state, autohybridization of the probe or probes places the fluorophore adjacent to the quencher, thereby quenching the fluorescent signal. However, under denaturing conditions, or when the beacon is hybridized to a complementary nucleic acid sequence, the fluorophore is separated from its quencher, and a fluorescent signal is detectable.

In the case of non-fluorogenic assays, however, reagents often are not available that will produce an altered fluorescence following the reaction of interest, i.e., there is no change in fluorescent quantum efficiency of the product from the substrate, or between the free and bound (or complexed) reactants. Thus, while a substrate may bear a detectable label, the products of the action of an enzyme on that substrate will bear the same label and be present in the same mixture, and are therefore not separately detectable without, for example, a subsequent separation step. The same is true, for example, where a ligand bears a detectable label, and is contacted with a receptor of interest in a mixture. The free ligand bears the same label as the ligand/receptor complex, and is therefore generally indistinguishable from the bound or complexed ligand/receptor in typical fluorescent intensity detection systems, without at least a subsequent separation step.

Despite these difficulties however, many reactions do result in changes in other properties of the reactants/products. For example, in many cases, a reaction will produce a change in charge and/or size of the reactants and/or products. As noted previously, because reactants and products of these non-fluorogenic assays cannot be distinguished from each other with respect to fluorescence intensity or spectrum, when present in a mixture of the two, it is generally necessary to separate them prior to detection.

As in bench scale operations, it is these changes in reactant characteristics that are exploited in separating the reactants and products in the microfluidic devices of the present invention. Specifically, the devices and systems of the present invention that are used in performing such non-fluorogenic assays, comprise an interconnected microfluidic channel structure that includes a reaction region and a separation region. In particularly preferred aspects, the devices include a channel portion in which reactants are maintained together, in order to allow the reaction to progress. Following the reaction, the unreacted reactants and the products are moved to a separation channel or channel portion, where separation of the reactants and products is carried out, followed by detection of the desired component, typically the product.

In addition to non-fluorogenic enzyme assays, a number of other assays are non-fluorogenic or non-chromogenic. For example, with the possible exception of assays that utilize a molecular beacon, e.g., certain nucleic acid binding assays, most binding assays are non-fluorogenic or non-chromogenic. In particular, the bound or complexed components of the assay do not change in the amount or spectrum of fluorescence over that of the free components. Thus, in a mixture the bound and free components are typically indistinguishable. Again, such assays typically utilize a separation step to first separate, then identify the relative levels of bound and free components. In most cases, such assays are carried out by tethering one member of the binding pair, e.g., the receptor or ligand, or one strand of complementary nucleic acids. The other binding member that bears a fluorescent label is then contacted with the tethered member, and the labeled material that does not bind is washed away, leaving the bound fluorescent, or otherwise labeled material to be detected. This is one of the basic principles behind the development of molecular array technologies. See, e.g., U.S. Pat. No, 5,143,854, to Pirrung et al. Alternatively, such assays would require the separation of bound and free components using, e.g., a chromatographic step.

The devices and systems of the invention are equally applicable to such binding assays, and utilize the same principles as outlined above. In particular, bound complexes often have different charges, sizes or charge:mass ratios from their separate reactant components. These differences are exploited, as described above, to separate the reactants, e.g., unbound labeled ligand and unbound receptors, from the products, e.g., complexed labeled ligand and receptor. The separated components are then separately detected, whereby their relative concentrations are determined.

Although described in terms of reactions that employ two or more reactants followed by separation of reactants and the products, it will be apparent that the methods and devices of the invention are readily employed in separating a product from the reactant in a single reactant reaction, e.g., where product is formed from the single reactant, e.g., a spontaneous reaction (degradation, association, aggregation, etc.), as a result of a thermal or photo-induced reaction (photolysis etc.).

Related methods are also described in PCT/US98/11969 (WO98/56956), and are incorporated herein by reference.

C. Devices, Systems and Methods

Integration of multiple different operations within a single microfluidic device can create a number of difficulties. For example, as noted above, there are a number of difficulties associated with accurately transporting microscale fluid volumes within integrated channel structures. However, even more problems arise where different operations to be performed within the microscale channels have markedly differing, and even conflicting goals. For example, in a number of analytical operations, in the reaction portion of the overall operation it is generally desirable to maintain all of the reactants in contact with one another, to ensure that the reaction will proceed. For the separation portion of the operation, however, it is generally necessary to separate those very same reactants from one another, and/or from their products.

As used herein, the terms "reactant" and "product" are not intended to denote any specific type of interaction, but are generally used to refer to an interaction between two or more chemical, biochemical or biological species, which interaction includes, chemical, biochemical, electrical, physical or other types of interactions. Some specific nonlimiting examples of reactants and their respective products include, e.g., complementary single stranded nucleic acids and their double stranded products, ligands and receptors, and the complexes formed therefrom, enzymes and substrates, and the products produced therefrom, cells and cell affectors and products of such interactions, e.g., agglutinated cells, secreted cellular products, cells with activated incorporated reporter systems, etc.

In its simplest embodiment, the operations carried out using the devices and systems of the invention are performed by providing a first channel into which the various reactants are introduced as a continuous mixture. After the reaction has been allowed to occur, a portion of the mixture is then aliquoted into a separate channel region in which separation of the reaction components occurs. Separation typically involves a chromatographic or electrophoretic separation of these components in the separation channel. The separated components are then detected at a detection window in the separation channel. Although described in terms of mixtures of reactants, it will be readily appreciated that the present invention is useful in performing integrated reaction and separation operations where a single reactant is introduced into the system. For example, photolyzable compounds that are first photolyzed, then separated, fall within the scope of "reactants" as defined herein. Similarly, heat labile compounds that dissociate (e.g., double stranded nucleic acids), degrade, or hydrolyze under elevated temperatures also fall within this scope.

Figure 3A:
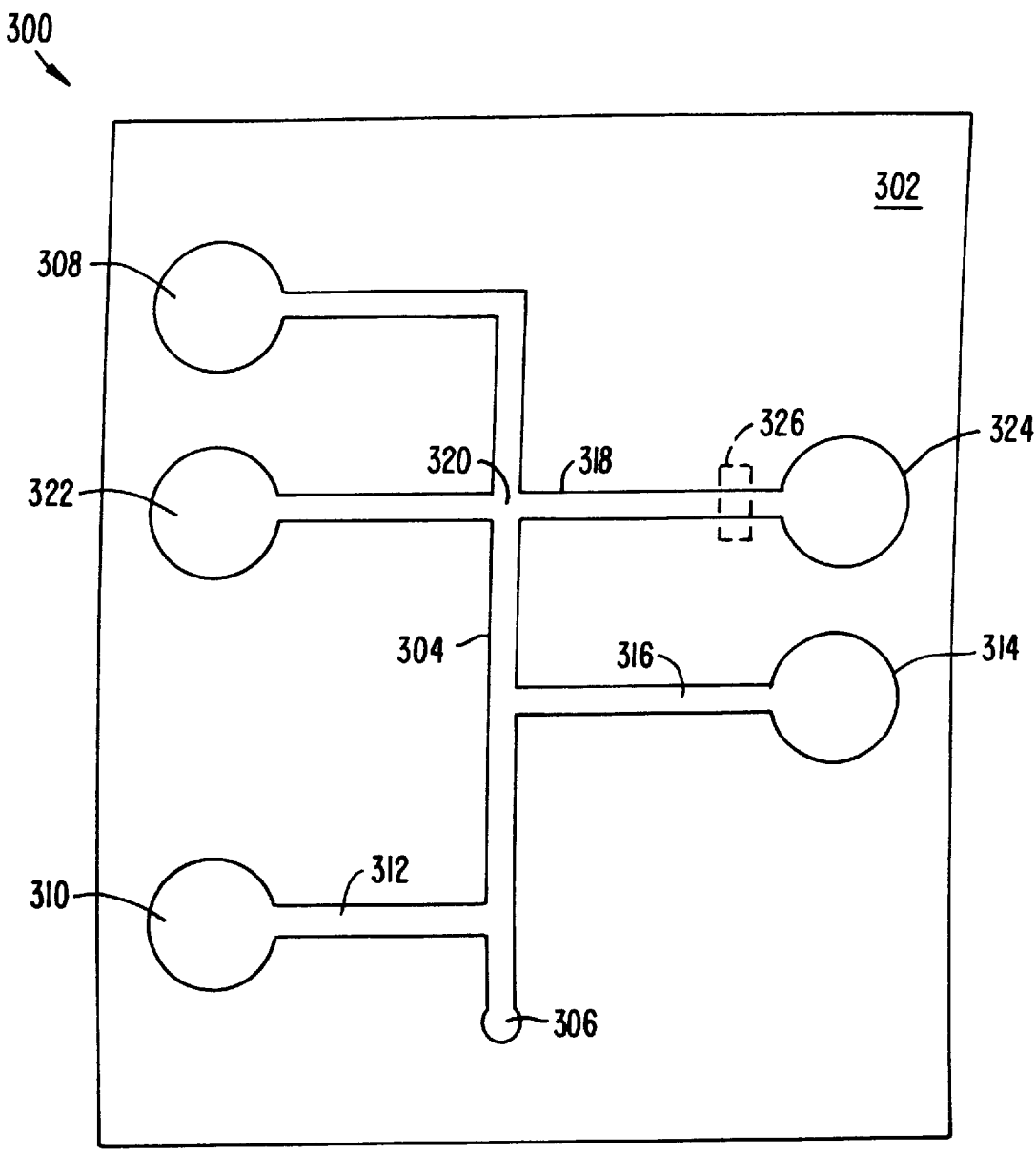
Figure 3A:
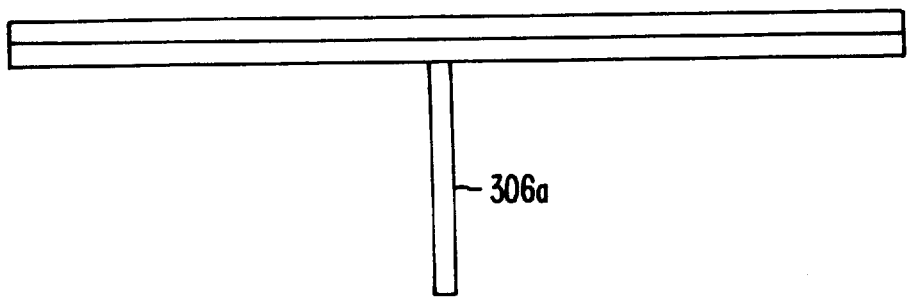
Figure 3B:
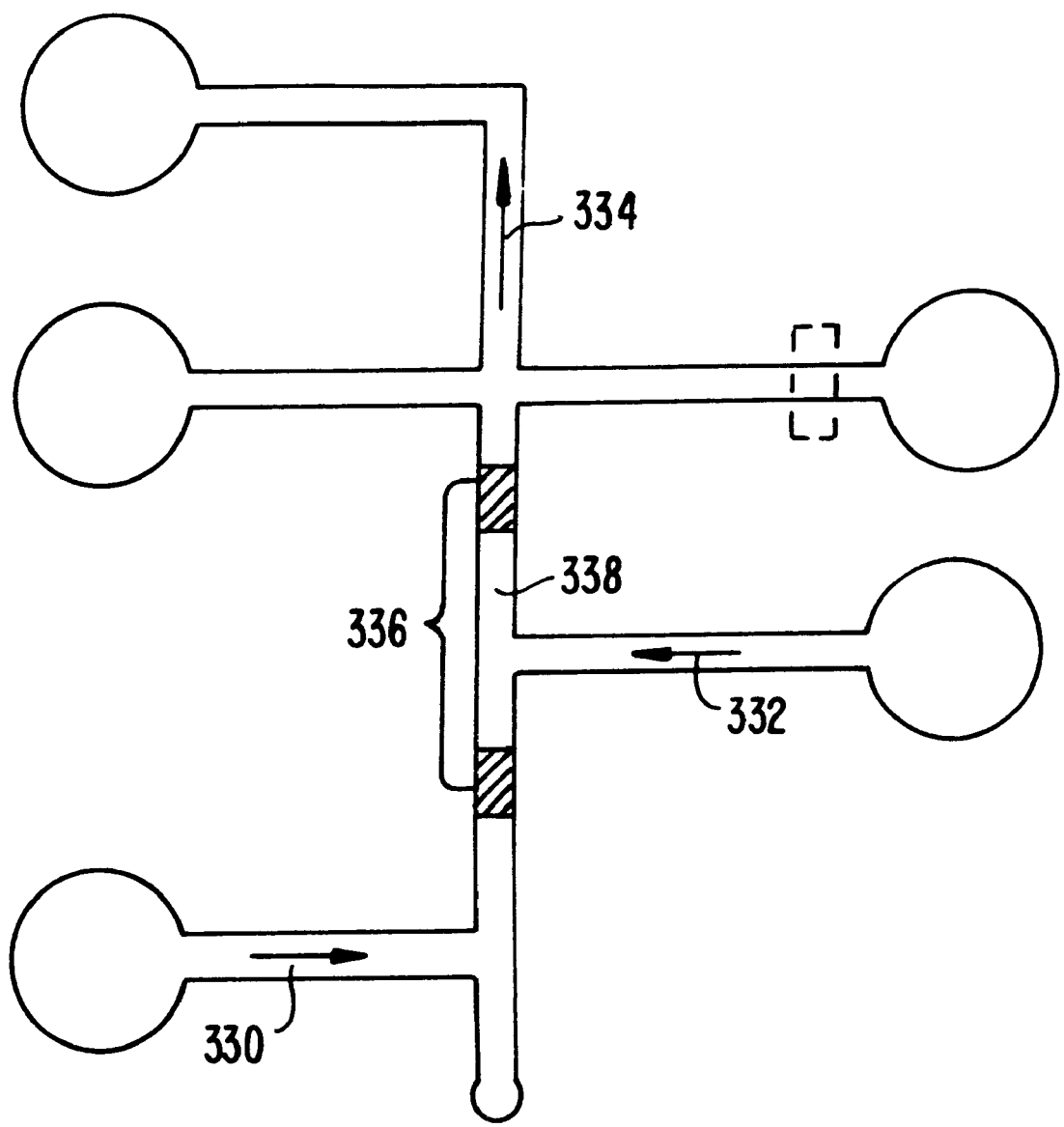
FIGS. 3B–3C illustrate the operation of the device in transporting, reacting and separating reaction components within the device of FIG. 3A.
Figure 3C:
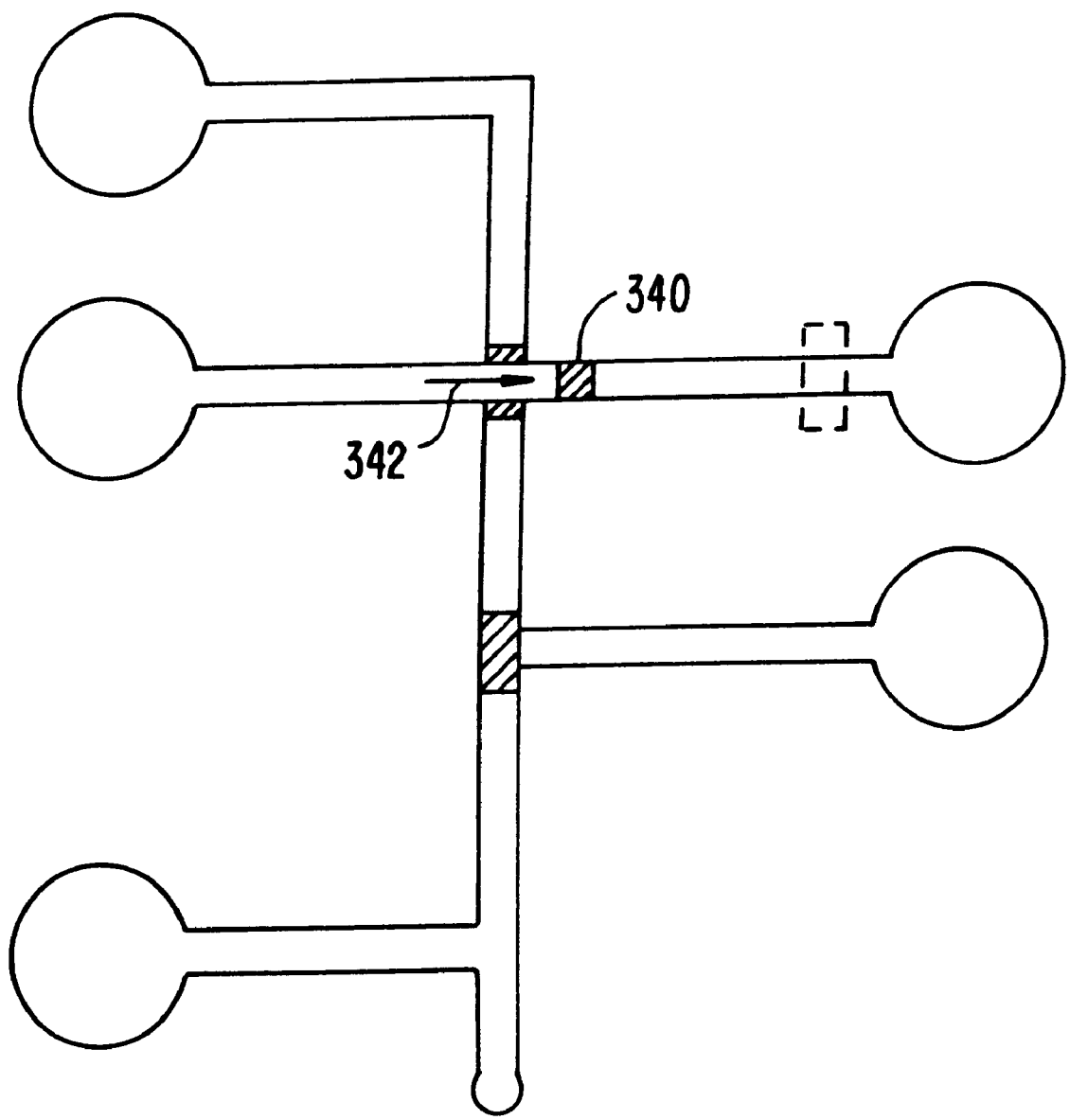

FIG. 3A schematically illustrates a microfluidic device for performing these integrated operations from a top and end view. FIGS. 3B and 3C illustrate the use of the device of FIG. 3A in an "injection mode," e.g., where reaction mixtures are injected into a connected channel. As shown in FIG. 3A, the device 300, includes a substrate 302 that includes a reaction channel 304 that connects a first reactant source and a waste reservoir 308. As shown, the first reactant source is shown as an inlet 306 from an external sample accessing capillary 306a, e.g., an electropipettor (See WO 98/00705). A second reactant reservoir 310 is fluidly connected to the reaction channel 304 via channel 312. A third reactant reservoir 314 is connected to the reaction channel 304 via channel 316. Separation channel 318 intersects and crosses the reaction channel 304 at a first intersection 320, and connects separation buffer reservoir 322 and waste reservoir 324. In operation, the first reactant is introduced into the reaction channel through the external sample accessing capillary 306a. The second reactant is flowed into the reaction channel from second reactant reservoir 310 via channel 312, whereupon it is mixed with the first reactant. An optional third reactant is introduced into reaction channel 304 from reservoir 314 via channel 316. The reaction mixture is flowed through the reaction channel 304 past the first intersection 320 and toward the waste reservoir 308.

A portion of this reaction mixture at the intersection 320 is then injected into the separation channel 318, which includes an appropriate buffer, medium or matrix for separating the components of the mixture. Typically, the separation medium is selected to permit the electrophoretic separation of the components of the reaction mixture, e.g., reactants and products. Generally, the separation medium is selected to substantially reduce the relative level of electroosmotic flow of fluid within the separation channel, leaving electrophoresis as the primary force in moving the materials, and through which differentiation of those materials is achieved. In most cases, it is sufficient that the separation medium comprises a buffer that includes an ionic strength that is sufficiently high, such that electrophoretic differentiation of species is allowed to occur in the channel, e.g., before electroosmotic flow transports the material into the waste reservoir. In some cases however, e.g., in the separation of larger macromolecules, electrophoretic differentiation of species is enhanced by the incorporation of a sieving component within the separation medium, e.g., a polymer matrix component. Examples of separation media incorporating such matrices have been widely described for use in capillary electrophoresis applications. See, U.S. Pat. No. 5,264,101 to Demorest, and U.S. Pat. No. 5,110,424 to Chin. Typically, sieving matrices are polymer solutions selected from, e.g., agarose, cellulose, polyacrylamide polymers, e.g., cross-linked or non-crosslinked polyacrylamide, polymethylacrylamide, polydimethylacrylamide, and the like. Useful separation matrices also include other types of chromatographic media, e.g., ion exchange matrices, hydrophobic interaction matrices, affinity matrices, gel exclusion matrices, and the like. Similarly, the types of separations performed in the separation channel can be varied to include a number of different separation types, e.g., micellar electrokinetic chromatography, isoelectric focusing chromatography, counter-current electrophoresis, and the like. In such cases, the products and reactants from which they are to be separated have different partitioning coefficients (vs. different electrophoretic mobilities) in the separation channel.

The portion of the reaction mixture that is injected into the separation channel is then transported along the separation channel allowing the components of the mixture to separate. These components are then detected at a detection window 326 at a point along the separation channel.

While the device and methods described above are useful for performing integrated reaction and separation operations, the throughput of the method as described, is somewhat limited. In particular, in the method described, only a single reaction is carried out in the reaction channel 304 at a time. After the separation of the reaction components has been carried out in the separation channel 318, new reaction components are introduced into the reaction channel for additional assays.

An alternate aspect of the present invention utilizes the same basic injection mode concept and device structure as that described with reference to FIG. 3A, and is illustrated in FIGS. 3B and 3C. This alternate aspect is designed to be utilized in conjunction with high-throughput screening assay methods and systems that utilize controlled electrokinetic material transport systems to serially introduce large numbers of compounds into a microfluidic channel in which a continuous flow assay is carried out. See, commonly assigned published International Application No. 98/00231, which is incorporated herein by reference in its entirety. In carrying out these high-throughput assays, one or more reactants are continuously flowed into the reaction channel 304 from reservoirs 310 and 314, as shown by arrows 330, 332 and 334. The compound materials (an additional set of reactants) are introduced from sampling capillary 306a, and are generally maintained together within discrete plugs 336 of material, to prevent smearing of one compound into the next which might result from electrophoretic movement of differently charged materials within the compound plug. These discrete plugs are then contacted with a continuously flowing stream of one or more additional reactants, e.g., enzyme and/or substrate, or members of specific binding pairs.

Maintaining the cohesiveness of the discrete compound/reactant plugs 336 (referred to as "reaction material plugs") in these flowing systems, and thus allowing them to react, is typically accomplished by providing the compound in a relatively high ionic strength buffer ("high salt buffer" or "high conductivity buffer"), and spacing the compound plugs with regions of low ionic strength buffer 338 ("low salt buffer" or "low conductivity buffer"). Because most of the voltage drop occurs across the low conductivity buffer regions rather than the high conductivity reaction material plugs, the material is electroosmotically flowed through the system before there can be extensive electrophoretic biasing of the materials in the compound plug 336. In order to subsequently separate the reactants and products resulting from the assay, as is often necessary in non-fluorogenic assays, the containing influence of the high salt plugs/low salt spacer regions must generally be overcome or "spoiled."

In accordance with the method described above, and with reference to FIG. 3C the containing influence of the high conductivity material plug 336/low conductivity spacer region 338, is overcome or spoiled by injecting a portion 340 of the high conductivity reaction material plug 336 into the separation channel 318 that is also filled with a high conductivity buffer, as the plug 336 moves past the intersection of the reaction channel and separation channel. As noted above, because the separation channel is filled with a high conductivity buffer, the electrokinetic mobility of materials within the channel resulting from the electrophoretic mobility of the components of the reaction material relative to the electroosmotic movement of the fluid is accentuated.

As the reaction material plug is transported past the intersection 320 of the reaction channel 304 and the separation channel 318, it is injected into the separation channel 318 by switching the flow through the separation channel, as shown by arrow 342. This is generally carried out by first slowing or halting flow of the reaction material plug through the reaction channel 304 while that plug 336 traverses the intersection 320. Flow is then directed through the separation channel to inject the portion of the plug that is in the intersection, into the separation channel 318. Controlling flow streams are also optionally provided at the intersection 320 during the reaction, injection and separation modes, e.g., pinching flow, pull-back flow, etc., as described above and in published International Application No. 96/04547, previously incorporated herein by reference.

Figure 3D:
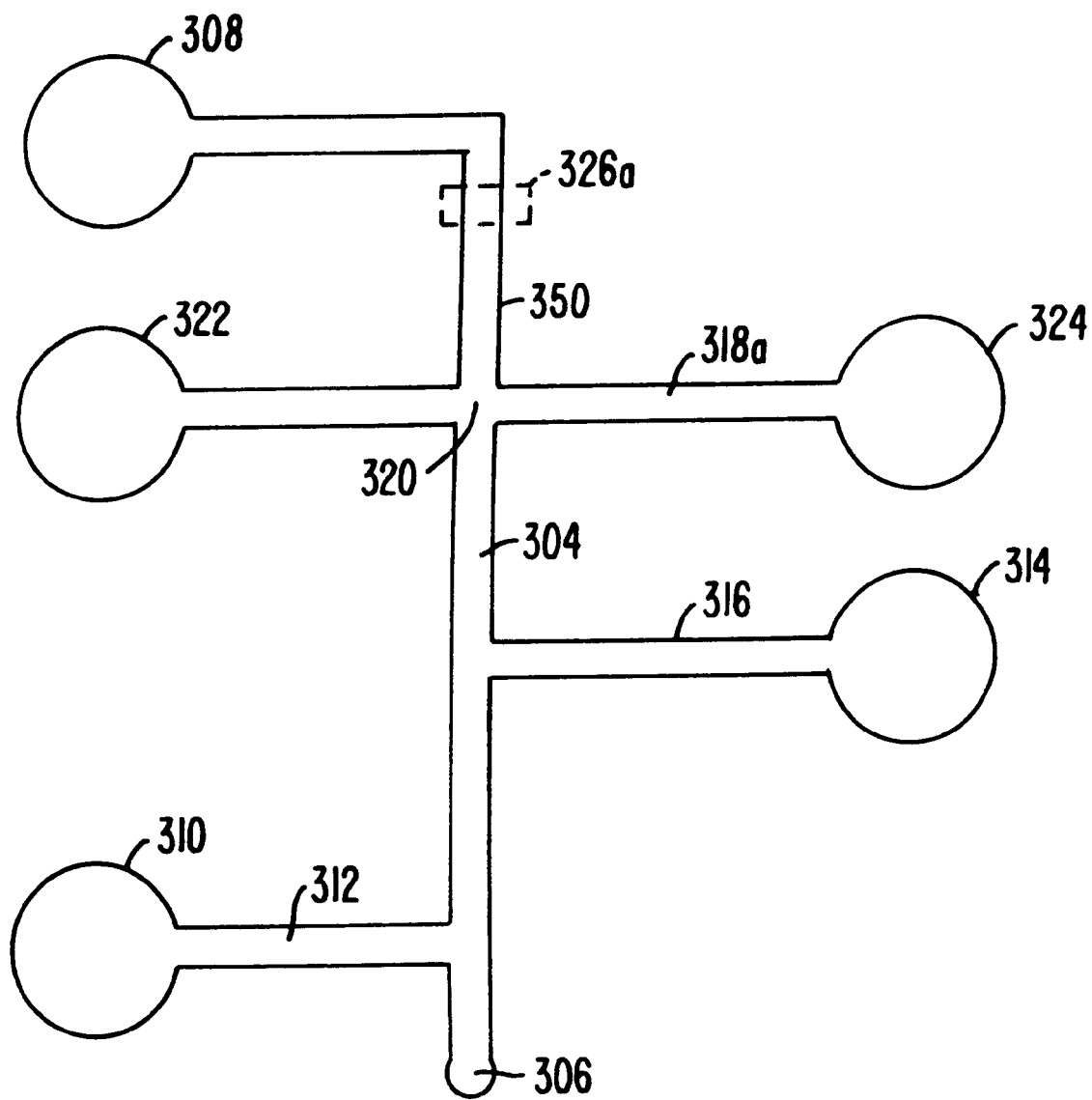
FIG. 3D illustrates an alternate configuration for the device shown in FIG. 3A.
Figure 3E:
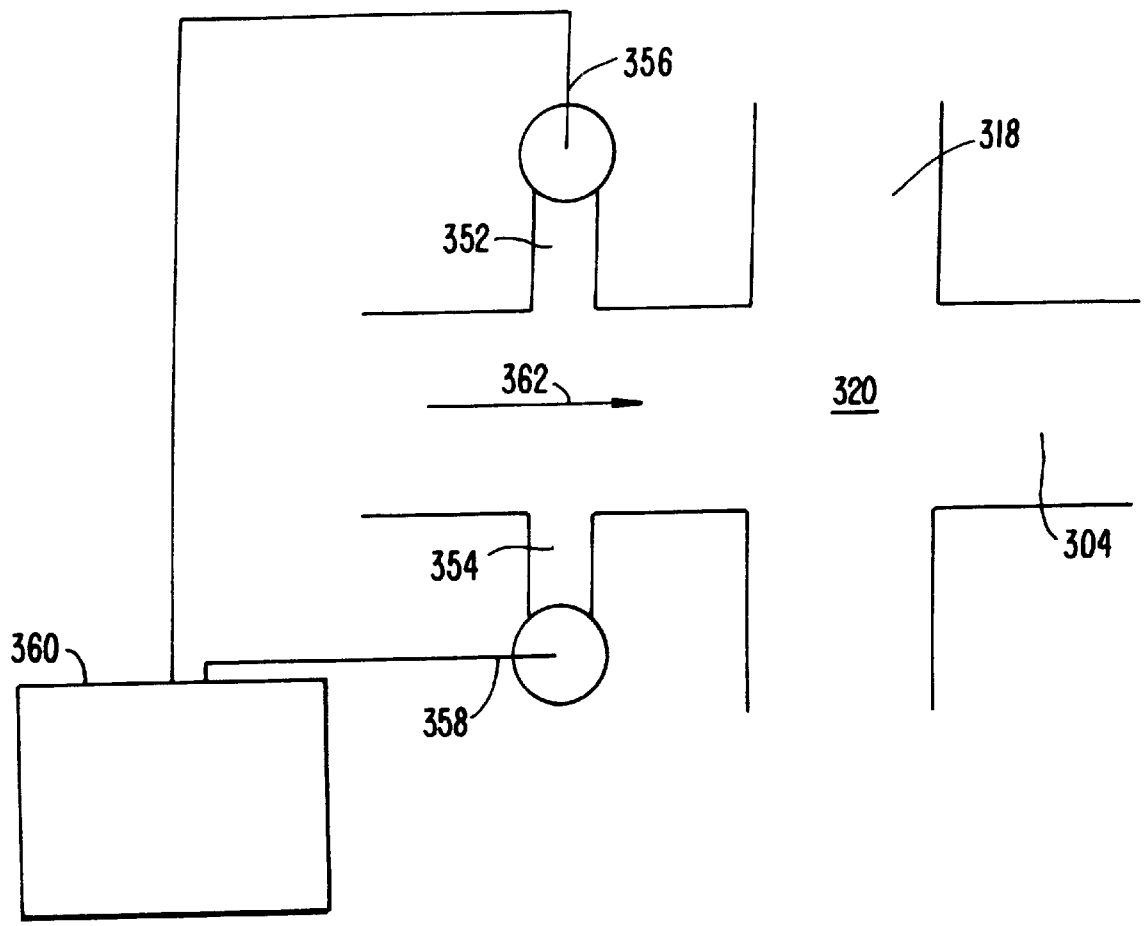
FIG. 3E illustrates a close-up view of an intersection in a device of the invention which incorporates conductivity measuring capabilities at the intersection for controlling injection of reaction mixtures into separation channels.

While this method is very effective, and is also applicable to high throughput systems, there is a measure of complexity associated with monitoring the progress of the reaction material plugs through the reaction channel and timing the injection of material into the separation channel. In one aspect, the passage of reaction material plugs through the intersection 320 is carried out by measuring the conductivity through the intersection, e.g., between reservoirs 322 and 324. In particular, because the reaction materials are contained in high ionic concentration plugs, their passage through the intersection will result in an increase in conductivity through the intersection and through the channel between reservoirs 322 and 324. Measurement of conductivity between reservoirs 322 and 324 is generally carried out using either a low level of direct current, or using an alternating current, so as not to disturb the electrokinetic flow of materials in the integrated channel network. Further, because electrokinetic transport is used, electrodes for measuring the conductivity through channels are already in place in the wells or reservoirs of the device. Alternatively, smaller channels are provided which intersect the reaction channel on each side, just upstream of the injection point or intersection, as shown in FIG. 3E. Specifically, channels 352 and 354 are provided just upstream of intersection 320, and include electrodes 356 and 358 in electrical contact with the unintersected termini of these channels. As used herein, the term "electrical contact" is intended to encompass electrodes that are physically in contact with, e.g., the fluid such that electrons pass from the surface of the electrode into the fluid, as well as electrodes that are capable of producing field effects within the medium with which they are in electrical contact, e.g., electrodes that are in capacitive contact or ionic contact with the fluid. These electrodes are then coupled with an appropriate conductivity detector 360 for measuring the conductivity of the fluid between the electrodes, e.g., in the reaction channel 304, as it flows into the intersection, which flow is indicated by arrow 362. Conductivity is then measured across these channels to identify when the reaction material plug is approaching the intersection. This conductivity measurement is then used to trigger injection of a portion of the reaction material plug into the separation channel 318. Typically, each of these additional channels includes a reservoir at its terminus distal to the reaction channel, and conductivity is measured via electrodes disposed in these reservoirs. Alternatively, the two detection channels could be provided slightly staggered so that the distance between the channels along the length of the reaction channel is small enough to be spanned by a single reaction material plug. The electrodes disposed at the termini of these channels are then used to sense the voltage difference between the intersection of each of the two channels and the reaction channel, e.g., along the length of the reaction channel. When a high conductivity reaction material plug spans the distance between the two channels, the voltage difference will be less, due to the higher conductivity of the fluid between them.

Another preferred method of addressing this issue is described with reference to FIG. 3D. In particular, as shown, the device has a similar layout to that of the device shown in FIG. 3A. However, in this aspect, the separation channel portion is channel portion 350, which is colinear with the reaction channel portion 304, channel portion 318a functions as a waste/gating channel, and the detection window 336a is disposed over channel portion 350. This method of transporting the material from the reaction channel region 304 to the separation channel region 350 is referred to as a "continuous flow mode" or "gated injection mode."

In operation, the reaction material plugs are directed along the reaction channel portion 304 through intersection 320, and into waste channel 318a, toward reservoir 324, e.g., using an electrokinetic gated flow. During operation of the device, the resistance level between reservoirs 322 and 324 is monitored. As a reaction material plug enters waste channel 318a, the increase in conductivity resulting from the higher ionic concentration of the high salt reaction material plug is used to trigger a gated injection of a portion of that plug into the separation channel 350. Specifically, upon sensing a predetermined level of conductivity increase, a computer linked with the electrical controller aspect of the overall system, directs a switching of the applied currents to produce the gated flow profile described above, for a short period, e.g., typically less than 1 second. By gating flow of the reaction material plugs into waste channel 318a, conductivity changes between reservoirs 322 and 324 are more pronounced as the length of the plug occupies a greater percentage of the channel across which the conductivity is being measured. As a result, one can more effectively identify meaningful conductivity changes and thereby determine when the reaction material plugs enter the intersection/injection point. Specifically, when using this latter method, one is measuring conductivity changes resulting from the length of the material plug, as opposed to measuring the changes resulting from the width of the plug, e.g., as it passes through an intersection across which conductivity is measured, as described with reference to FIGS. 3B–3C, above. Again, as described with reference to FIG. 3E above, auxiliary channels and reservoirs may be used to measure conductivity changes across different portions of a channel or intersecting channels, e.g., one conductivity sensing electrode may be placed in contact with the reaction channel, e.g., via a side channel, upstream of the intersection while another is placed downstream of the intresection.

Although described in terms of detecting changes in conductivity, a number of methods can be used to detect when the reaction material plug is present in or near the intersection. For example, marker compounds may be provided within either the reaction material region or the spacer regions. These compounds, and thus the presence or absence of a reaction material plug or region then can be detected at or near the injection intersection to signal a change in the flow profile from reaction to injection mode, e.g., injecting the reaction material into the separation channel portion. Such marker compounds optionally include optically detectable labels, e.g., fluorescent, chemiluminescent, colorimetric, or colloidal materials. The marker compounds are typically detected by virtue of a different detectable group than that used to detect the results of the reaction of interest. For example, where the reaction of interest results in a fluorescent product that must be separated from a fluorescent reactant prior to detection, the marker compound typically includes either a non-fluorescent compound, e.g., colored, colloidal etc., or a fluorescent compound that has a excitation and/or emission maximum that is different from the product and/or reactant. In the latter case, the detection system for detecting the marker compound is typically configured to detect the marker compound without interference from the fluorescence of the product/reactant label.

In preferred aspects, these marker compounds are neutral (have no net charge) at the operating pH of the system, so that they are not electrophoretically biased during transport within their discrete regions. Except as described above, these optically detectable marker compounds are typically detected using a similar or identical detection system used to detect the separated elements of the reaction of interest, e.g., a fluorescent microscope incorporating a PMT or photodiode, or the like.

Figure 4A:
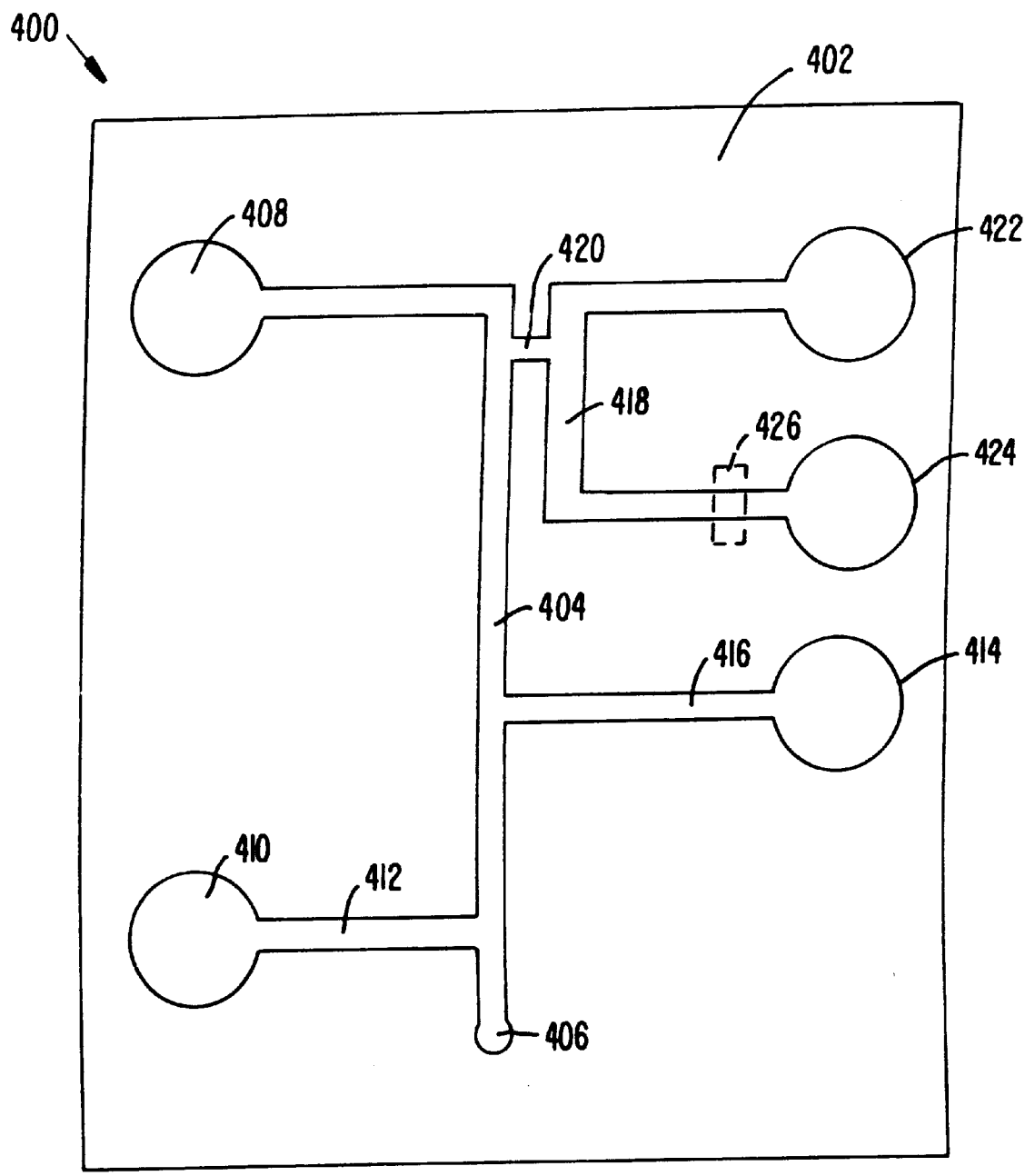

FIG. 4A schematically illustrates an alternative mechanism for overcoming the influence of these high salt plug/low salt spacer regions within the separation region or channel of the device using another version of the injection mode. As shown, the device 400, includes a substrate 402, having a reaction channel 404 disposed therein. As shown, the reaction channel 404 is in communication at one end with the inlet from a pipettor capillary 406 (shown from a top view). The pipettor 406 is capable of accessing and introducing large numbers of different sample materials into the analysis channel 404. The analysis channel is in communication at the other end, with a waste reservoir 408.

Reservoirs 410 and 414 typically include the different reactants needed for carrying out the reaction operation for the device and are connected to reaction channel 404 via channels 412 and 416, respectively. Separation channel 418 is located adjacent to analysis channel 404, and connecting channel 420 links the two channels at an intermediate point in both channels. Separation channel 418 links separation buffer reservoir 422 and waste reservoir 424. A detection window 426 is also provided within separation channel 418, through which separated sample components may be detected.

Figure 5:
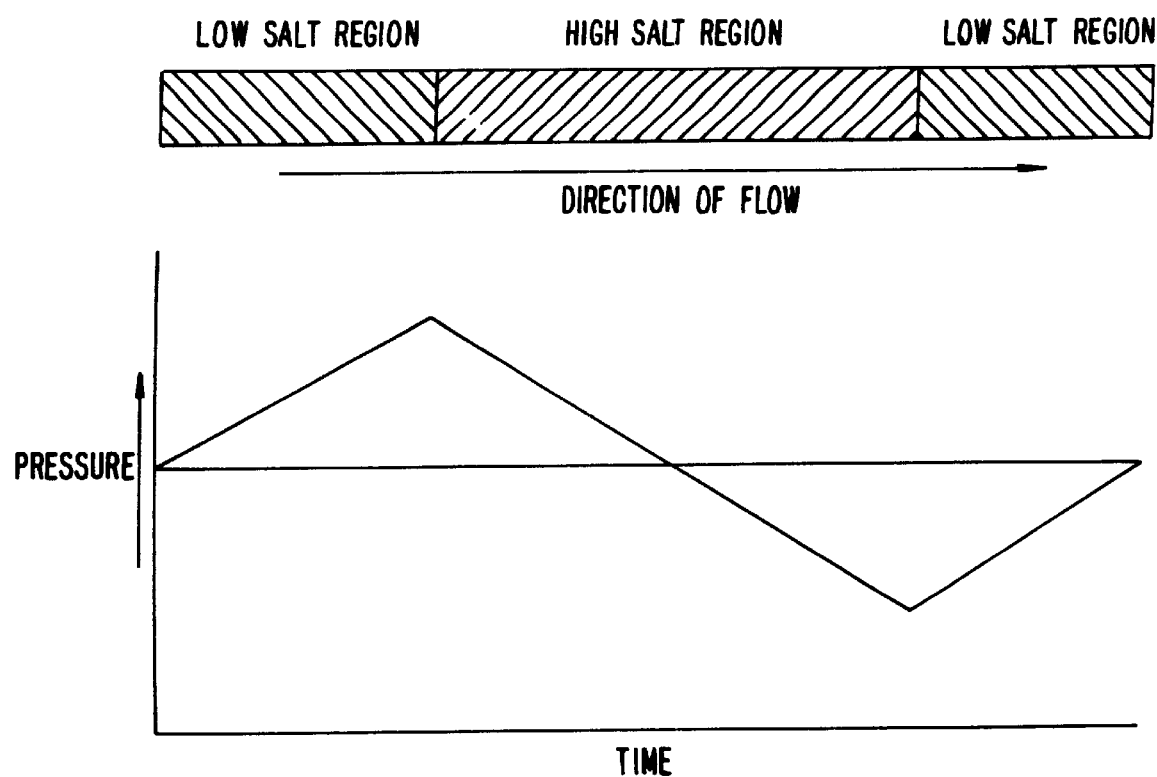
FIG. 5 is a schematic illustration of the pressure profile across fluid regions of differing ionic concentration when being transported through a microscale channel by electrokinetic forces.

In one mode, the device shown in FIG. 4 is capable of taking advantage of certain flow characteristics of fluids under electrokinetic transport. In particular, in electrokinetically moving different fluid regions that have different electroosmotic flow rates, pressure gradients are created within the fluid regions. In particular, electroosmotic fluid flow within a microscale channel is driven by the amount of voltage drop across a fluid region. Thus, low ionic strength, e.g., low conductance, high resistivity, fluid regions have higher electroosmotic ("EO") flow rates, because these regions drop a larger amount of voltage. In contrast, higher ionic strength fluids, e.g., higher conductance materials, drop less voltage, and thus have lower EO flow rates.

Where a system includes different fluid regions having different ionic strengths, these different flow rates result in pressure differentials at or near the interface of the two fluid regions. Specifically, where a first fluid of higher ionic strength, e.g., a sample material, is being pushed by a second fluid region of lower ionic strength, the trailing end of the first fluid region is at a higher pressure from the force of the second fluid region. Where the first fluid region is following the second fluid region, the pulling effect of the second fluid region results in a lower pressure region at the leading edge of the first fluid region. A channel that includes alternating high and low ionic strength fluid regions, will also include alternating high and low pressure areas at or near the interfaces of the different regions. FIG. 5 schematically illustrates the pressure gradients existing in a channel having such different ionic strength regions. These pressure effects were described and a method for overcoming them set fort in commonly owned published International Application No. WO 98/00705, incorporated herein by reference in its entirety. In brief, in order to prevent perturbations resulting from these pressure effects at channel intersections, the channel intersecting the main channel is typically made shallower, as the pressure effects drop off to the third power with decreasing channel depth, whereas electroosmotic pumping is only reduced linearly with channel depth. See Published International Application No. WO 98/00705.

Figure 4B:
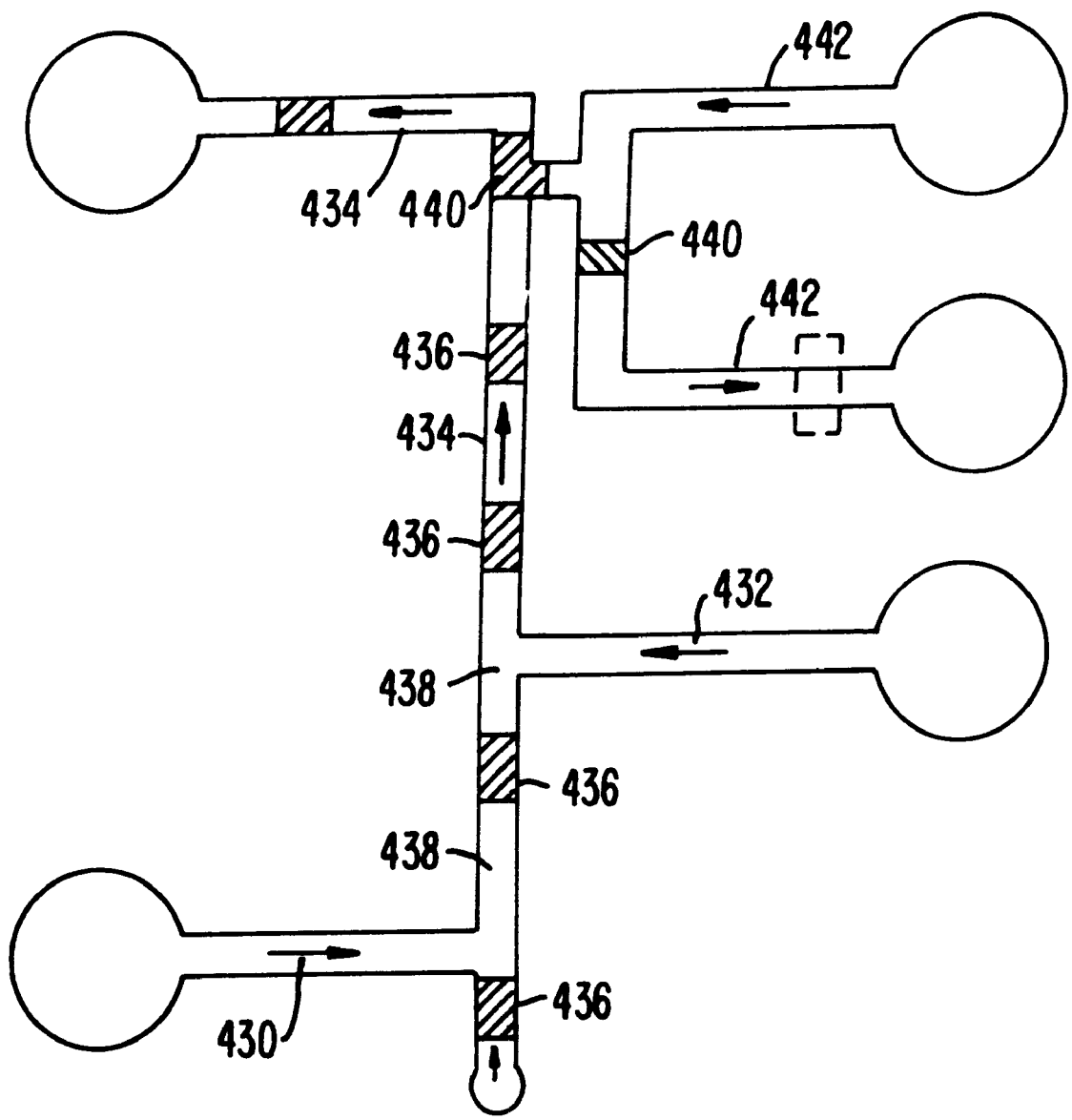
FIG. 4B illustrates the operation of the device in transporting, reacting and separating reaction components within the device of FIG. 4A.

The operation of the device shown in FIG. 4A is described below, with reference to FIGS. 4A and 4B in the performance of a high-throughput screening assay, which screens for affectors of a reaction of two reactants, e.g., inhibitors or enhancers of enzyme activity, inhibitors or enhancers of ligand receptor binding, or any other specific binding pair. In brief, the reactants are maintained in a relatively low ionic strength buffer, and are placed into the first reactant reservoir 410, and the second reactant reservoir 414. Each of these reactants is then electrokinetically transported through the reaction channel 404 toward waste reservoir 408 in a continuous stream, as indicated by arrows 430, 432 and 434. This electrokinetic transport is carried out, as described above, by applying appropriate voltage gradients between: (1) the first reactant reservoir and the waste reservoir; and (2) the second reactant reservoir and the waste reservoir.

Periodically, a plug of material 436 that includes a compound which is to be screened for an effect on the reaction of the two reactants is introduced into the reaction channel by way of the external sample accessing capillary 406 shown from an end view. The capillary 406 is integrated with the reaction channel 404. In particularly preferred aspects, this external sample accessing capillary 406 is an electropipettor as described in published International Patent Application No. WO 98/00705.

As described above, these plugs 436 of compound material are in a relatively high ionic strength buffer solution, and are introduced with spacer regions 438 of relatively low ionic strength buffer. The higher ionic strength compound plugs typically approach physiological ionic strength levels, and are preferably from about 2 to about 200 times the conductivity of the low ionic strength buffer, in some cases, from about 2 to about 100 times the conductivity of the low ionic strength buffer, and more preferably, from about 2 to about 50 times the conductivity of the low ionic strength buffer, and in many cases from about 2 to about 20 or even 10 times the conductivity of the low ionic strength buffer. Typically, the high ionic strength buffer has a conductivity from about 2 mS to about 20 mS, while the low ionic strength buffer has a conductivity of from about 0.1 mS to about 5 mS, provided the low ionic strength buffer has a lower conductivity than the higher ionic strength buffer.

As the plugs of material 436 are transported along the reaction channel, the two reactants are allowed to react in the presence of the compound that is to be screened, within the plug 436, and in the absence of the compound to be screened, outside of the plug 436, e.g., within spacer region 438. As the reaction material plug 436 moves past the intersection of reaction channel 404 and connecting channel 420, the pressure wave caused by the differential flow rates of the high ionic strength plugs and low ionic strength spacer regions causes a small portion of the material plug, or "aliquot," 440 to be injected into the connecting channel 420.

As shown in FIG. 5, the pressure wave caused by the interface of the high salt and low salt regions is reciprocated at the opposite interface of the next compound plug. As such, it is important to transport the aliquot 440 through the connecting channel 420 into the separation channel 418 and away from the intersection of these channels, before it is sucked back into the reaction channel 404. This is generally accomplished by providing the connecting channel with appropriate dimensions to permit the aliquot to progress entirely through the connecting channel and into the separation channel. Typically, the connecting channel will be less than 1 mm in length, preferably less than 0.5 mm in length, more preferably, less than 0.2 mm in length, and generally, less than about half the width of the reaction channel, e.g., typically from about 5 to about 100$\mu$m. Additionally, to prevent refluxing of the aliquot into the reaction channel, flow is typically maintained within the separation channel to move the aliquot 440 away from the intersection of connecting channel 420 and separation channel 418, which flow is indicated by arrows 442. This same injection process is repeated for each compound plug that is serially introduced into the reaction channel. The effects of the pressure wave at the intersection, and thus the size of the injected plug can be adjusted by varying the depth of the connecting channel at the intersection, as described above. For example, smaller injections are achieved by making the connecting channel shallower than the reaction channel.

The separation buffer within separation channel 418 is selected so as to permit separation of the components within the aliquot of reaction material. For example, whereas the materials in the reaction channel are contained in a high salt plug to prevent electrophoresis, the separation channel typically includes a high salt buffer solution, which then allows the electrophoretic separation of the components, e.g., by diluting the low salt regions and their effects on material movement in the channels, e.g., increased electroosmotic flow as compared to the electrophoretic effects on the components of the reaction material. Of course, in some cases, a high salt buffer is used in order to create a more uniform conductivity throughout the separation channel, allowing separation of components in the aliquot of reaction material before the material is electroosmotically transported out of the separation channel.

As described, in alternate or additional aspects, the separation channel includes a separation matrix, or sieving polymer, to assist in the separation of the components of the reaction material aliquot.

Once the reaction material is injected into the separation channel 418 it is transported through the separation channel and separated into its component elements. Typically, the flow of material within the separation channel is directed by electrokinetic means. Specifically, a voltage gradient is typically applied between separation buffer reservoir 422 and waste reservoir 424, causing the flow of material through the separation channel. In addition, the voltage gradient within the separation channel 418, is typically applied at a level whereby there is no current flow through the connecting channel 420, or only sufficient current to prevent leakage through the connecting channel during non-injection periods. This prevents the formation of any transverse currents between the separation channel and the reaction channel, which might disturb controlled material flow. Once separated, the components of the reaction material are then transported past a detection window 426 which has an appropriate detector, e.g., a fluorescence scanner, microscope or imaging system, disposed adjacent to it.

Optionally, the device illustrated in FIG. 4 employs active material transport, e.g., electrokinetic transport, to inject a portion 440 of the reaction material plug 436 into the separation channel 418. In particular, the reaction material plug 436 is electrokinetically transported along the reaction channel 404, as described above. Once the reaction material plug 436 reaches the intersection of the reaction channel 404 and the connecting channel 420, the electrical potentials at the various reservoirs of the device are switched to cause current flow, and thus, flow of a portion of the reaction material, through the connecting cannel, into the separation channel 418. The portion 440 of the reaction material plug is then electrokinetically transported through separation channel 418 by virtue of current flow between the reservoirs 422 and 424. The current through the separation channel is adjusted to match the current flowing through the reaction channel 404, so that no transverse currents are set up through the connecting channel. This active electrokinetic injection, as well as the more passive pressure differential injection described above, provide advantages over other injection modes of integrated reaction an separation, by permitting the reaction and separation channels to operate at the same time. Specifically, transport of material along the reaction channel does not need to be arrested during the separation process, and vice versa.

Figure 6A:
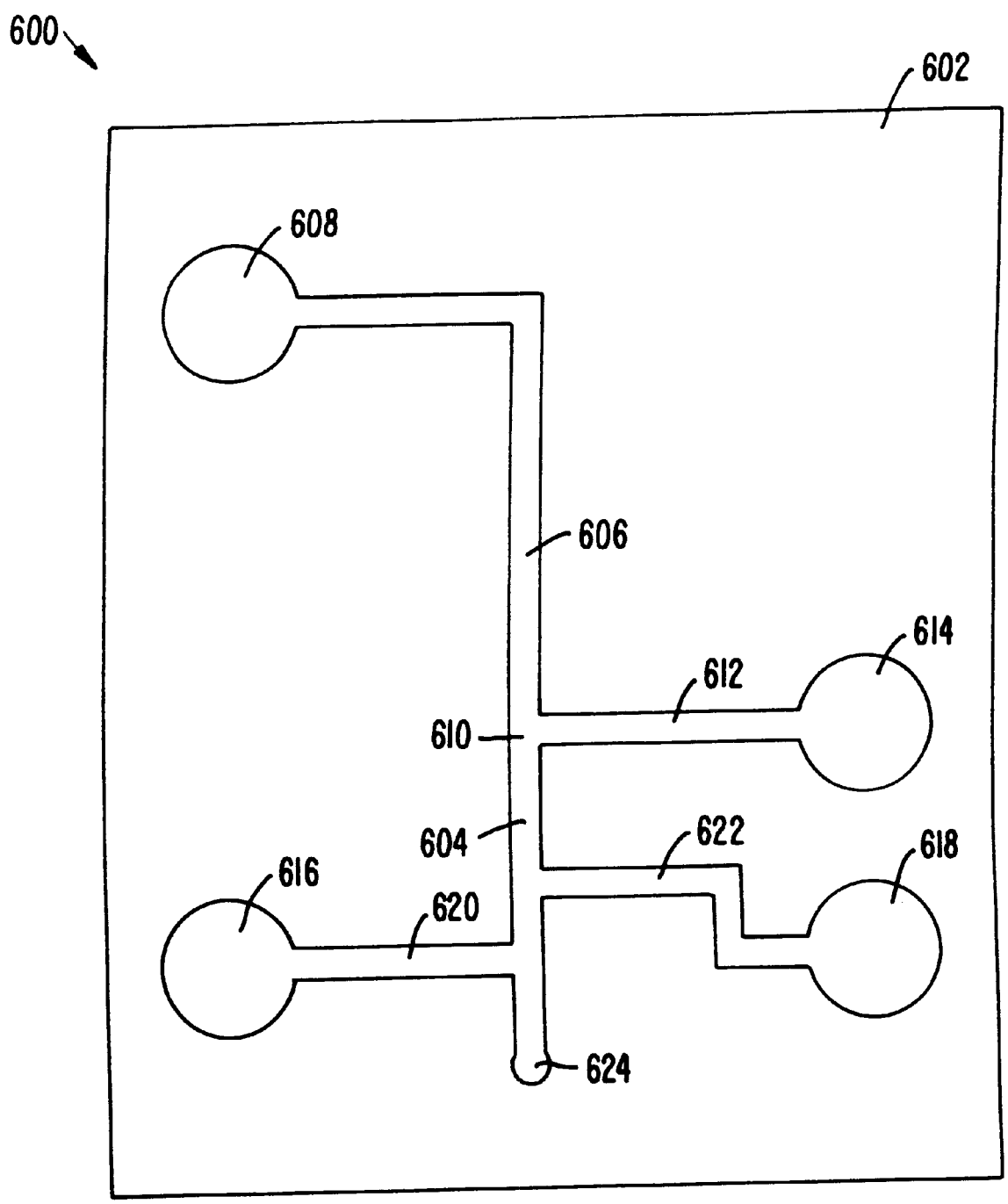
FIG. 6A schematically illustrates the structure of the device itself, while FIG. 6B schematically illustrates the operation of the device.
Figure 6B:
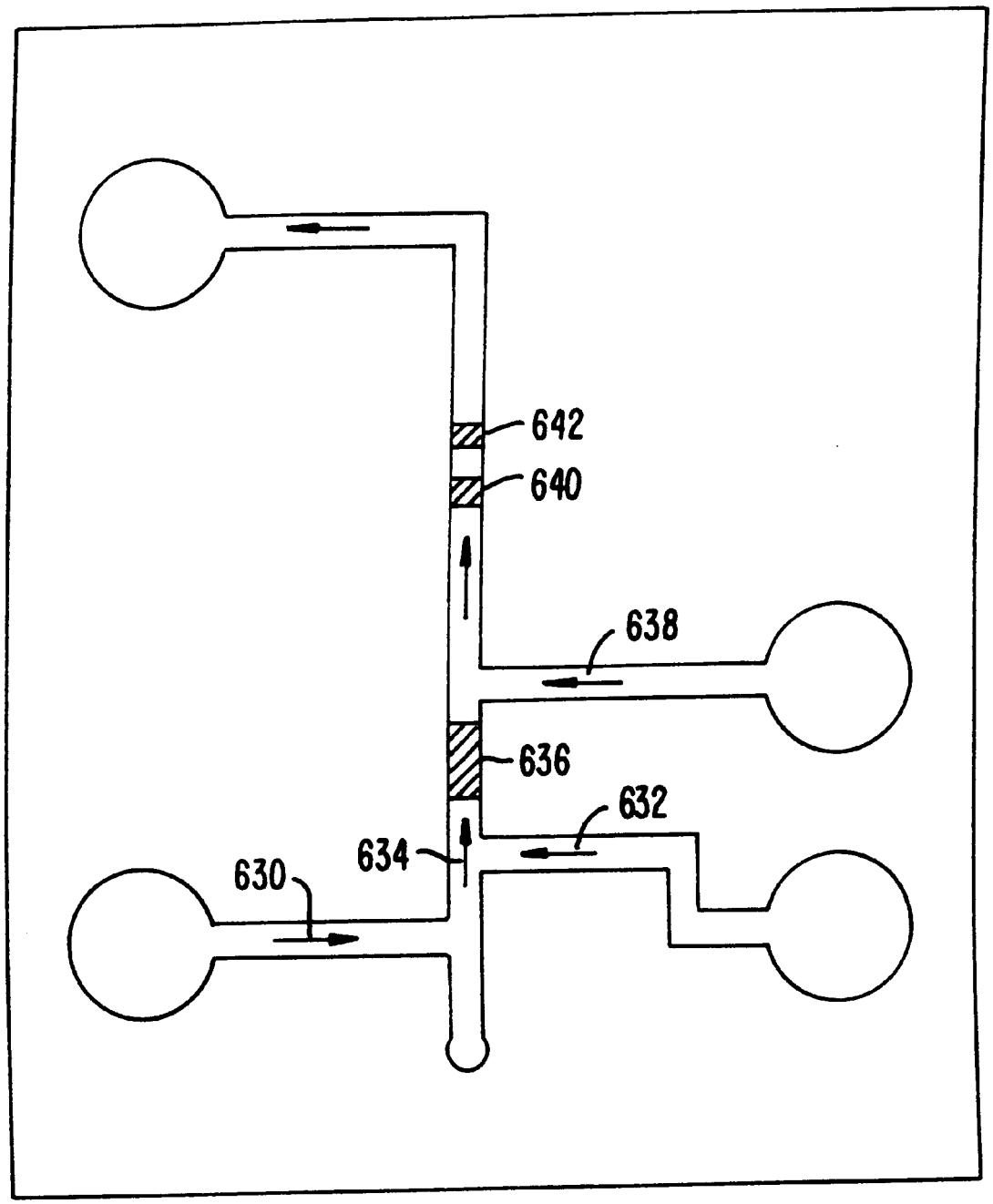
FIG. 6 illustrates an alternate device for performing a contained reaction operation followed by a separation operations in a continuous flow mode.

A simpler embodiment of the present invention and particularly a microfluidic device for carrying it out, is illustrated in FIG. 6. In this embodiment, the containing influence of the high salt plugs in the reaction region or channel of the device, as described above, is overcome or spoiled by introducing a stream of separation inducing buffer into the system at the junction between the reaction and separation regions. As used herein, the term "separation inducing buffer" refers to a buffer in which molecular species may be readily separated under appropriate conditions. Such buffers can include pH altering buffers, sieving buffers, varied conductivity buffers, buffers comprising separation inducing components, e.g., drag enhancing or altering compounds that bind to the macromolecular species to create differential separability, and the like. For example, in the systems of the present invention, the separation inducing buffer generally refers to either a high salt or low salt buffer introduced into the system at the junction point between the reaction and separation regions. The introduction of high salt or low salt buffer lessens the conductivity difference between the reaction material plug (typically in high salt buffer) and the spacer region (typically in low salt buffer), by diluting out or spoiling the differential electrophoretic/electroosmotic forces among the different regions. This dilution or spoiling allows electrophoretic separation of the materials in the plug, as described above. This method is referred to as a "continuous flow mode" because the reaction material plugs are continuously flowing along a colinear channel, without being redirected into an intersecting channel. Typically, the separation inducing buffer will be either: (1) a high salt buffer having a conductivity that is greater than the conductivity of the low salt buffer regions, e.g., from about 2 to about 200 times greater, preferably from about 2 to about 100 times greater, more preferably, from about 2 to about 50 times greater, and still more preferably, from about 2 to about 20 times greater, and often from about 2 to about 10 times greater than the conductivity of the low salt buffer regions; or (2) a low salt buffer having a conductivity that is lower than the first conductivity by the same factors described above. Of course, implied in these ranges are separation inducing buffers that have conductivity that is substantially approximately equivalent to either of the high salt fluid regions or low salt fluid regions.

As shown in FIG. 6A, the device 600 is disposed in a planar substrate 602, and includes a reaction channel region 604 and a separation channel region 606. The reaction and separation channels are in communication at a junction point 610. Waste reservoir 608 is disposed at the terminus of the separation channel region 606. Also intersecting these channels at the junction point 610, is an additional channel 612 which delivers high conductivity buffer from reservoir 614 into the separation channel region. As with the device described above, reactants are delivered into the junction point 610 for reaction channel region 604 and separation channel region 606, from first and second reactant reservoirs 616 and 618 via channels 620 and 622. Compounds that are to be screened for effects on the reaction of the reactants are typically introduced using an appropriate external sample accessing capillary or pipettor 624, e.g. an electropipettor.

In operation, the reactants are transported from their respective reservoirs 616 and 618 and along the reaction channel region 604 in a continuous flow stream, as indicated by arrows 630, 632 and 634. Periodic plugs of compounds to be screened 636 in high salt buffer are also flowed along the reaction channel, the reaction mixture of the first and second reactants and the test compound being contained within the high salt plug 636 and adjacent low salt regions. As the plug of material 636 is transported past the junction point 610, a stream of higher conductivity buffer, indicated by arrow 638, continuously mixes with the reaction mixture plug and adjacent low ionic strength regions changing the relative field strengths across the high and low ionic strength regions, e.g., the voltage drop across the lower ionic strength regions is decreased. This change in field strengths allows differentially charged material components within the reaction mixture plug 636 to be separated into their component species 640 and 642, based upon differences in the electrophoretic mobility of those components, as they move along the separation channel region 606. It should be noted that in accordance with the present invention, a lower salt buffer could also function as a "spoiling buffer" to bring the relative ionic strengths of the different material regions closer together, and expose the entire length of the channel to similar voltage gradients, e.g., including the components of the reaction mixtures.

Figure 10A:
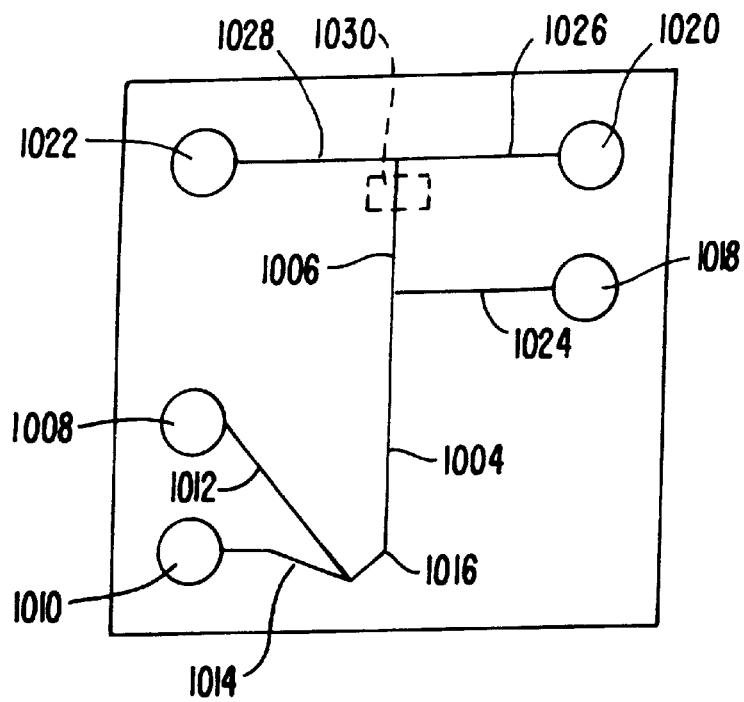
Figure 10B:
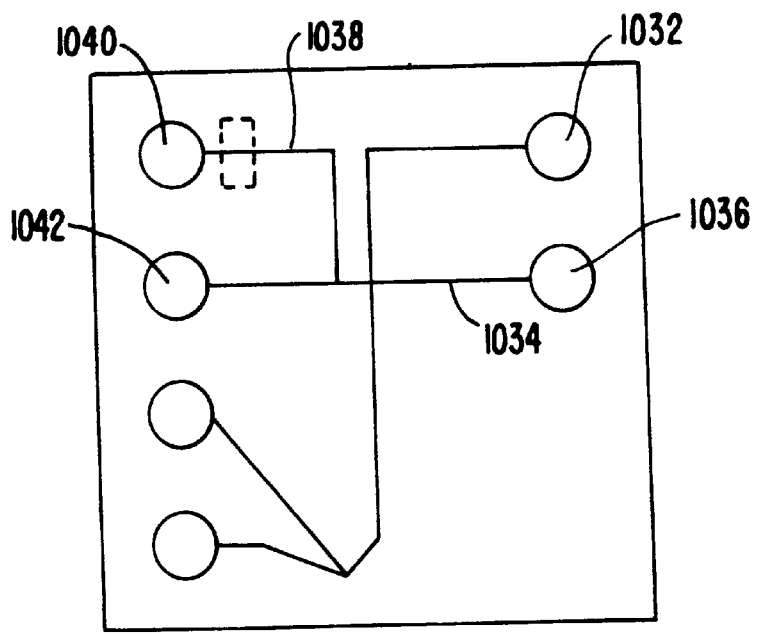
FIG. 10b illustrates an alternate device which includes a separate but connected channel in which electrokinetic separations are carried out.

Examples of a device and system for performing integrated reaction/separation operations using a combination of pressure flow and electrokinetic transport are schematically illustrated in FIGS. 10*a* and 10*b*.

As shown in FIG. 10*a*, the device 1000 includes a body structure 1002 which includes a first channel portion 1004 that is fluidly connected to a second channel portion 1006. The first channel portion is also fluidly connected to sources of reactants 1008 and 1010, via channels 1012 and 1014, respectively. The first channel portion is also shown in fluid connection with an external capillary element (not shown) via port 1016. As shown, the second channel portion 1006 is fluidly connected to ports/reservoirs 1018, 1020, and 1022 via channel portions 1024, 1026 and 1028, respectively. As shown, the device 1000 also includes a detection window 1030 disposed across the second channel portion 1006.

In operation, first and second analytes, e.g., enzyme and substrate, ligand and receptor, etc., are introduced into the first channel portion 1004, from reservoirs 1008 and 1010, via channels 1012 and 1014, respectively. The first and second analytes are moved into the first channel portion by applying an appropriate pressure differential between the reservoirs and the first channel. In the device shown, this is optionally accomplished by applying a vacuum to reservoir 1022, which is translated into the first channel portion 1004 by channels 1028 and 1006. A third analyte is introduced into the first channel portion 1004 through the capillary element (not shown) via inlet port 1016. Again, the vacuum applied to the system functions to draw material that is placed into contact with the open end of the capillary element. Specifically, the capillary element is dipped into a source of at least a third reactant whereby the vacuum sips the reactant into the capillary channel and into channel portion 1004. The first, second and optionally third reactants are permitted to react as they move along the first channel portion 1004 toward the intersection with channel portion 1006. As no electric field is applied across this channel portion 1004, no electrophoretic separation of the reactants and/or their products will occur.

Once the reaction mixture moves into channel portion 1006, it is subjected to an electric field to promote electrophoretic separation of the species therein. The electric field is typically applied across channel portion 1006 by placing electrodes into contact with fluid that is disposed in reservoirs 1020 and 1018, creating an electric field between the reservoirs and across channels 1024, 1006, and 1026. As the reaction components separated, the separation is detected at detection window 1030, typically as a fluorescent signal, or deviation from a steady state fluorescent signal.

An alternate device construction for carrying out the same assay methods is illustrated in FIG. 10*b*. Components of the device shown in FIG. 10*b* that are the same as those shown in FIG. 10*a* are referenced with the same reference numerals. As shown, the device 1000 includes a first channel portion 1004 that is fluidly connected to at least first and second reactant sources, e.g., reservoirs 1008 and 1010, and includes the optional inlet port 1016 fluidly coupled to an external capillary element (not shown). The first channel portion is fluidly coupled to a vacuum port/reservoir 1032. An additional channel 1034 intersects and crosses the first channel portion 1004 and is fluidly connected to reservoir/port 1036.

As with the device illustrated in FIG. 10*a*, a second channel portion 1038 is used to perform the separation operation. The separation channel portion connects reservoirs 1040 and 1042, and is fluidly connected to channel portion 1004 via channel 1034.

In operation, the reaction mixture, as described with reference to FIG. 10*a*, is drawn into the first channel portion by applying a vacuum to reservoir/port 1032. The reaction mixture then moves across the intersection of channel portion 1004 and channel 1034. A portion of the reaction mixture at this intersection is then injected into the second channel portion 1038. Injection of the reaction mixture from the first channel portion 1004 into the second channel portion is preferably accomplished by applying an electrical filed across channel 1034, e.g., between reservoir/port 1036 and 1042 or 1040. Once a plug of the reaction mixture is introduced into the second channel portion, application of an electric field across the second channel portion 1036, e.g., between reservoirs 1042 and 1040, then causes the electrophoretic separation of the different reaction components, thereby allowing their detection at detection window 1030. One of the advantages this latter channel structure offers over that shown in FIG. 10*a* is the ability to inject discrete plugs of reaction mixture into the separation channel. In particular, only a small volume of reaction material is injected into the second channel portion for separation. However, this adds complexity when performing higher throughput assays, which are typically simpler in a continuous flow system, e.g., as shown in FIG. 10*a*.

The invention is further described with reference to the following nonlimiting examples.

EXAMPLES

Figure 7:
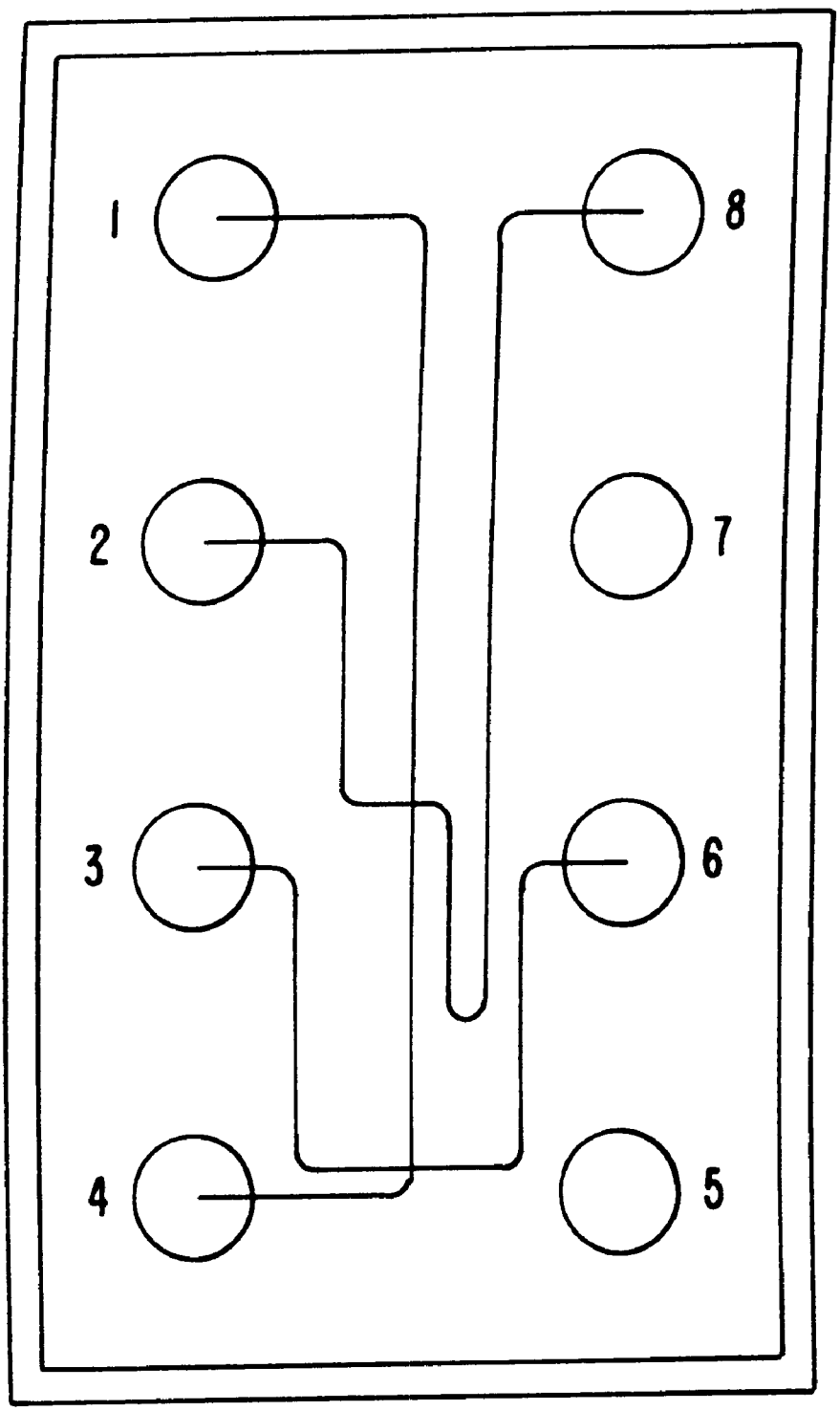
FIG. 7 illustrates a microfluidic device channel layout used in performing integrated operations where the first portion of the operation requires containment of reactants while the second portion requires their separation.

The following examples demonstrate the efficacy of the methods and devices of the present invention in performing integrated containment or reaction and separation operations. For these examples, a microfluidic device having the channel geometry shown in FIG. 7 was used. In these experiments, a low salt buffer containing 50 mM HEPES at pH 7.5, and a high salt buffer containing 50 mM HEPES+ 100 mM NaCl at pH 7.5 were prepared. A second high salt buffer ("ultra high salt buffer"), containing 50 mM HEPES+ 200 mM NaCl at pH 7.5, was prepared and used as the "spoiling buffer" in the continuous flow mode. A neutral dye, Rhodamine B, and an anionic dye, Fluorescein, were placed in the high salt buffer in well 3 of the device shown in FIG. 7, and used as markers to track electrophoretic containment and separation in all experiments, because these dyes have different electrophoretic mobilities.

Example 1

Continuous Flow Mode Reaction/Separation

In the continuous flow mode, e.g., as described above with reference to FIG. 7, above, the buffer wells of the device shown in FIG. 7 were loaded as follows: low salt buffer was loaded in wells 1 and 4, high salt buffer with dyes was loaded in well 3, high salt buffer was loaded in well 6, and ultra high salt buffer was loaded in wells 2 and 8. The following voltages and currents were applied to the listed wells, to direct movement of the materials through the device using an eight channel current based electrical controller which included a series of pin electrodes inserted into the wells:

| 1 | 2 | 3 | 4 | 5 | 6 | 7 | 8 | Time(s) | Flow Profile |
|---|---|---|---|---|---|---|---|---|---|
| 500 V | 10 μA | 0 μA | 0.5 μA | 0 V | 0 μA | 0 V | 10 μA | 20 | Fill channel w/low salt |
| 500 V | 0 μA | 0 μA | −7 μA | 0 V | 10 μA | 0 V | 0 μA | 4 | Create guard bands |
| 500 V | 0 μA | 10 μA | −7 μA | 0 V | 0 μA | 0 V | 0 μA | 1 | Inject sample |
| 500 V | 10 μA | 0 μA | 0.5 μA | 0 V | 0 μA | 0 V | 10 μA | 10 | Move sample down channel/separate |

Figure 8:
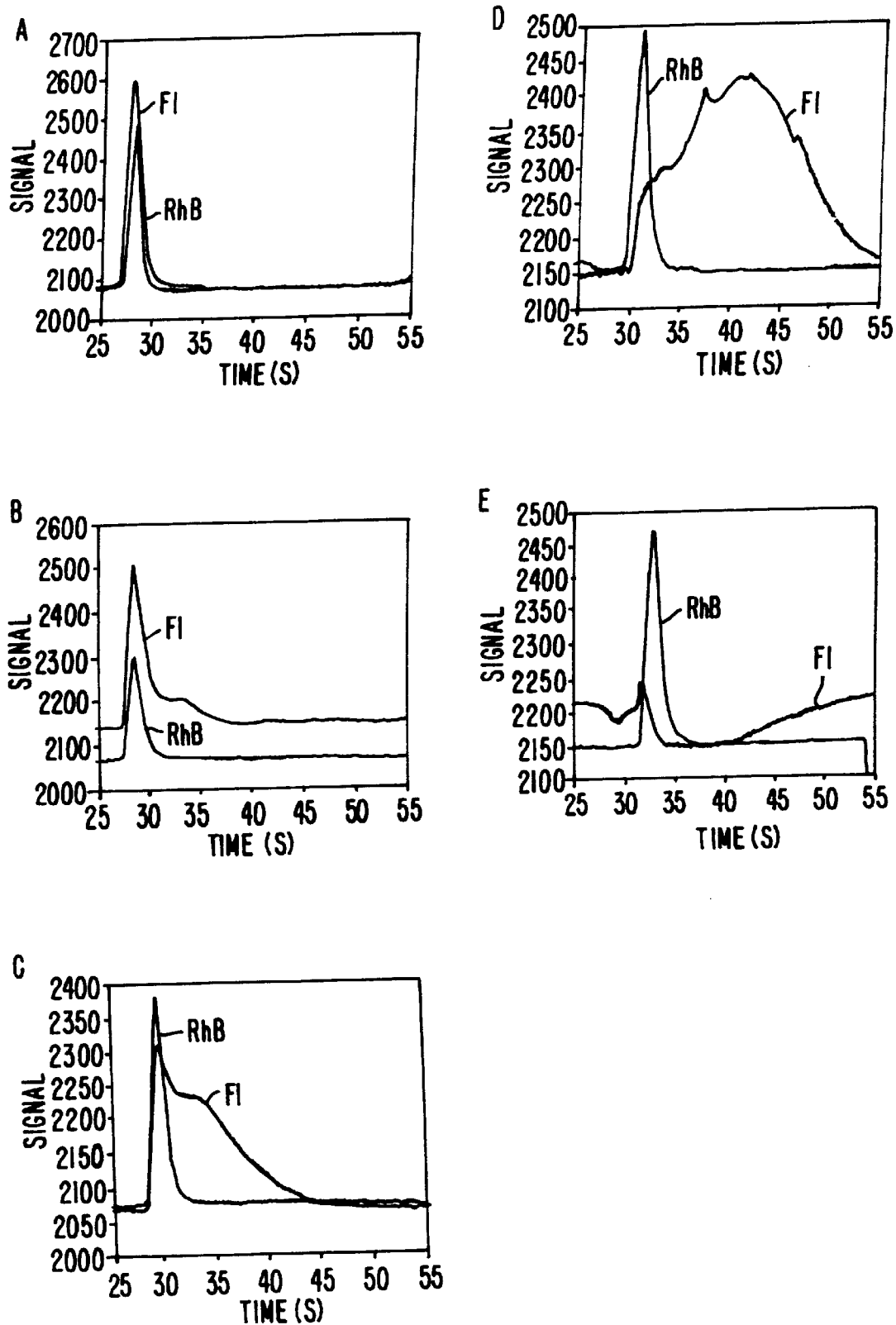
FIG. 8 illustrates the fluorescence signal of rhodamine B and fluorescein monitored at various locations along the main channel during the continuous flow mode operation using the device shown in FIG. 7.

To monitor the degree of containment and separation of dyes, the location of the detection point was varied along the channel path of dye flow, and the plotted signals for each detection point are provided in the panels of FIG. 8. This series of plots clearly indicate that the dyes are contained in the high-low salt format before the injection point (Panel A). The containment is successfully disrupted, e.g., the containing influence is overcome, upon the addition of the spoiling buffer into the main channel, leading to separation of dyes downstream (Panels B, C, D and E).

Example 2

Injection Mode

In the injection/separation flow mode, the wells were loaded as follows: low salt buffer in wells 1 and 4, high salt buffer with dyes in well 3, high salt buffer in wells 6, 2, and 8. Controlling currents and voltages were applied as follows:

| 1 | 2 | 3 | 4 | 5 | 6 | 7 | 8 | Time(s) | Flow Profile |
|---|---|---|---|---|---|---|---|---|---|
| 500 V | 0 μA | 0 μA | 3 μA | 0 V | 0 μA | 0 V | 0 μA | 10 | Fill channel w/low |
| 500 V | 0 μA | −.5 μA | −7 μA | 0 V | 10 μA | 0 V | 0 μA | 4 | Create guard bands |
| 500 V | 0 μA | 10 μA | −7 μA | 0 V | 0 μA | 0 V | 0 μA | 2 | Inject sample |
| 500 V | 0 μA | 0 μA | 3 μA | 0 V | 0 μA | 0 V | 0 μA | 2.8 | Move sample down main channel |
| 0 μA | 10 μA | 0 μA | 0 μA | 0 V | 0 μA | 0 V | 100 V | 0.5 | Cross inject sample into second channel |
| 500 V | 0 μA | 0 μA | 3 μA | 0 V | 0 μA | 0 V | 0 μA | 10 | Clear main channel |
| −.5 μA | 10 μA | 0 μA | 0 μA | 0 V | 0 μA | 0 V | 100 V | 60 | Move sample down separation channel |

Figure 9:
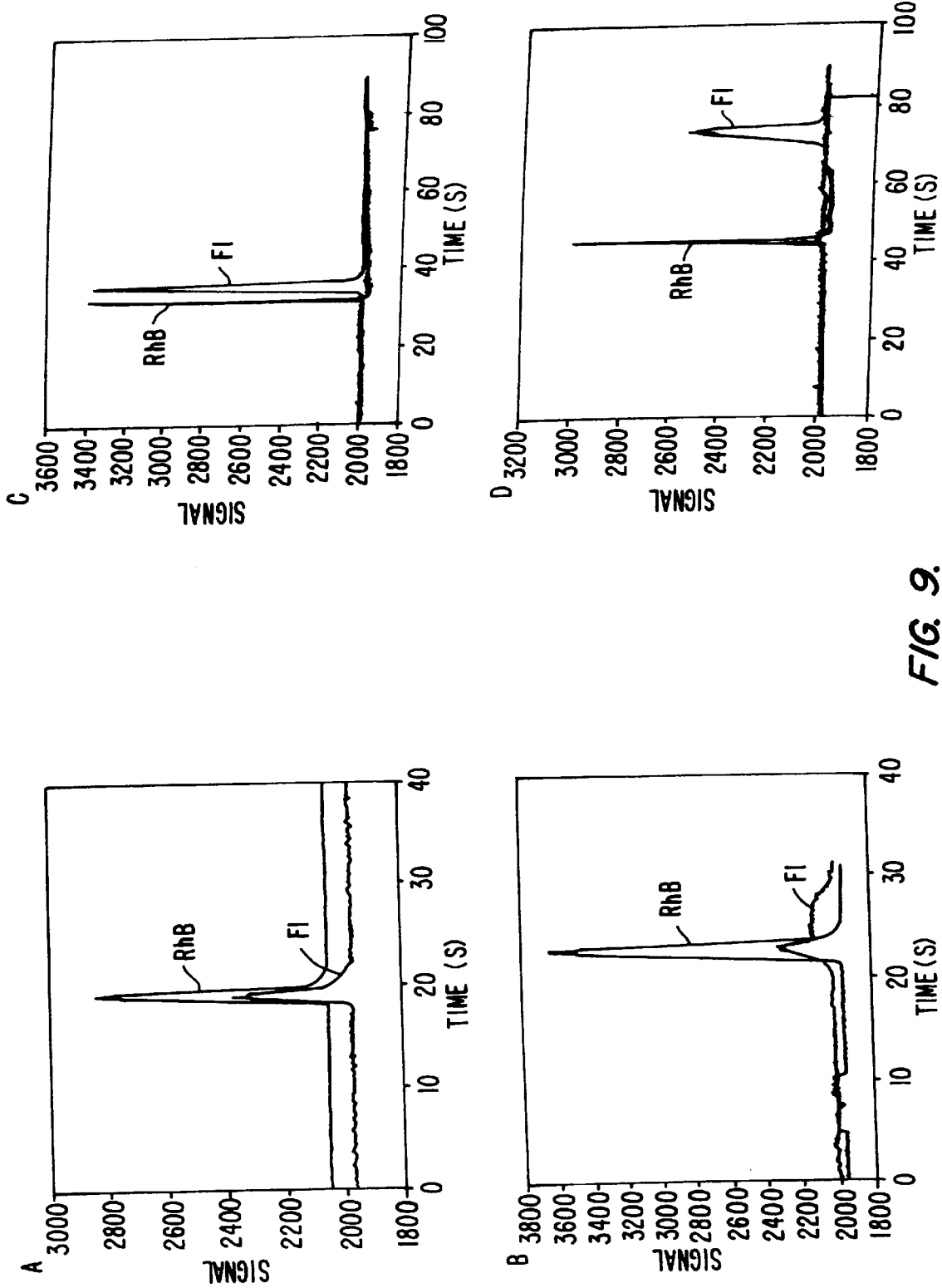
FIG. 9 illustrates the fluorescence signal of rhodamine B and Fluorescein monitored at various locations along the main channel and separation channel during the injection mode operation using the device shown in FIG. 7.

The location of the detection point along the main and separation channels again was varied to monitor the degree of containment of the two dyes. FIG. 9 summarizes the results of the dye signals graphically. Once again, the dyes were clearly contained in the high-low salt format before the injection point, (panels A and B) and were cleanly separated by electrophoresis in the separation channel (panels C and D).

In summary, these experimental results demonstrated the feasibility of both the continuous flow and stop flow approaches for integrating electrophoretic containment and electrophoretic separation in the same microfluidic device.

The discussion above is generally applicable to the aspects and embodiments of the invention described in the claims.

Moreover, modifications can be made to the methods apparatus and systems described herein without departing from the spirit and scope of the invention as claimed, and the invention can be put to a number of different uses including the following.

The use of a microfluidic integrated system or device for performing any of the methods and assays set forth herein, particularly the use of the devices and integrated systems set forth herein for performing any of the assays or methods set forth herein.

The use of any microfluidic system or device as described herein for performing integrated reaction and separation operations, mobility shift operations, or any other operation set forth herein, e.g., for analysis of one or more analytes, as set forth herein.

Use of an assay or method utilizing a feature or operational property of any one of the microfluidic systems or devices described herein, e.g., for practicing any method or assay set forth herein.

Use of kits comprising any device, device element, or instruction set, e.g., for practicing any method or assay set forth herein, or for facilitating practice of any method or use of any device or system set forth herein, including maintenance kits for maintaining the devices or systems herein in an appropriate condition to practice the methods and assays set forth herein. While the foregoing invention has been described in some detail for purposes of clarity and understanding, it will be clear to one skilled in the art from a reading of this disclosure that various changes in form and detail can be made without departing from the scope of the invention. For example, all the techniques and apparatus described above may be used in various combinations which will be apparent upon complete review of the foregoing disclosure and following claims. All publications and patent applications listed herein and the references cited within those documents are hereby incorporated herein by reference to the same extent as if each individual publication or patent application was specifically and individually indicated to be incorporated by reference. Although the present invention has been described in some detail by way of illustrations and examples for purposes of clarity and understanding, it will be apparent that certain changes and modifications may be practiced within the scope of the appended claims.

What is claimed is:

1. A method of analyzing an effect of a first analyte on a second analyte, comprising:
    contacting a first analyte with a second analyte in continuous flow mode in a first microfluidic channel portion having substantially no electric field applied across its length, wherein the first analyte and the second analyte interact to produce a product;

transporting at least a portion of the first analyte, second analyte and product to a second channel portion that is in fluid communication with the first channel portion and which has an electric field applied across its length;

detecting a difference in the electrokinetic mobility of the product relative to at least one of the first and second analytes, the difference in mobility being indicative of an effect of the first analyte on the second analyte.

2. The method of claim 1, wherein the effect of the first analyte on the second analyte is a binding of the first analyte to the second analyte, thereby producing a product with a different electrokinetic mobility relative to the first analyte or the second analyte.

3. The method of claim 1, wherein the effect of the first analyte on the second analyte is a cleavage effect, thereby producing a product with a different electrokinetic mobility relative to the first analyte or the second analyte.

4. The method of claim 1, wherein the product comprises a detectable label.

5. The method of claim 4, wherein the detectable label comprises an optically detectable label.

6. The method of claim 5, wherein the optically detectable label comprises a fluorescent label.

7. The method of claim 1, wherein the first analyte, the second analyte and the product are transported into the second microfluidic channel portion by applying a pressure differential between the first channel portion and the second channel portion.

8. The method of claim 1, wherein the difference in electrokinetic mobility results from a change in charge of the product relative to the first or second analytes.

9. The method of claim 1, wherein the first analyte is transported from a first reservoir into the first channel portion, and the second analyte is transported from a second reservoir into the first channel portion, thereby contacting the first analyte with the second analyte in the first microfluidic channel portion.

10. A method of detecting the effect of a third analyte on the interaction between a first and a second analyte, the method comprising:

contacting a first analyte and a second analyte with at least one third analyte in a first microfluidic channel portion having substantially no electric field applied across its length, wherein the first analyte and the second analyte interact to produce a product;

transporting at least a portion of the first analyte, second analyte and product to a second channel portion that is in fluid communication with the first channel portion and which has an electric field applied across its length;

detecting a difference in the electrokinetic mobility of the product relative to at least one of the first and second analytes, the difference in mobility being indicative of an effect of the first analyte on the second analyte; and, measuring a change in the electrokinetic mobility of the product in the presence of the at least one third analyte relative to a change in the electrokinetic mobility of the product in the absence of the at least one third analyte.

11. The method of claim 10, wherein the first analyte is transported from a first reservoir into the first channel portion, and the second analyte is transported from a second reservoir into the first channel portion, thereby contacting the first analyte with the second analyte in the a first microfluidic channel portion.

12. The method of claim 10, comprising contacting the first, second and third analytes in a high-throughput screening format.

13. The method of claim 10, comprising contacting the first, second and third analytes in continuous flow mode.

14. The method of claim 10, comprising contacting the first and second analytes and periodically introducing a plurality of third analytes into a continuously flowing stream comprising the first and second analytes.

15. The method of claim 10, wherein the at least one third analyte comprises a test compound.

16. The method of claim 10, wherein the at least one third analyte comprises an affector of a reaction.

17. The method of claim 16, wherein the affector is an inhibitor or an enhancer.

18. The method of claim 10, wherein the first and second analytes are selected from the group comprising: an enzyme and a substrate, a ligand and a receptor, and a cell affector and a cell.

19. The method of claim 10, wherein the product comprises a detectable label.

20. The method of claim 19, wherein the detectable label comprises an optically detectable label.

21. The method of claim 20, wherein the optically detectable label comprises a fluorescent label.

22. The method of claim 10, wherein the first analyte, the second analyte and the product are transported into the second microfluidic channel portion by applying a pressure differential between the first channel portion and the second channel portion.

* * * * *

UNITED STATES PATENT AND TRADEMARK OFFICE
CERTIFICATE OF CORRECTION

PATENT NO.     : 6,551,836 B1                                      Page 1 of 1
DATED          : April 22, 2003
INVENTOR(S)    : Andrea W. Chow et al.

It is certified that error appears in the above-identified patent and that said Letters Patent is hereby corrected as shown below:

<u>Column 28,</u>
Line 16, before "first" delete "a".

Signed and Sealed this

Sixteenth Day of September, 2003

JAMES E. ROGAN
*Director of the United States Patent and Trademark Office*